(12) United States Patent
Ben-David et al.

(10) Patent No.: US 7,778,702 B2
(45) Date of Patent: Aug. 17, 2010

(54) COMBINED PARASYMPATHETIC STIMULATION AND DRUG THERAPY

(75) Inventors: Tamir Ben-David, Tel Aviv (IL); Omry Ben-Ezra, Tel Aviv (IL); Ehud Cohen, Ganei Tikva (IL)

(73) Assignee: Bio Control Medical (B.C.M) Ltd., Yehud (IL)

( * ) Notice: Subject to any disclaimer, the term of this patent is extended or adjusted under 35 U.S.C. 154(b) by 99 days.

(21) Appl. No.: 11/975,240

(22) Filed: Oct. 17, 2007

(65) Prior Publication Data
US 2008/0125843 A1 May 29, 2008

Related U.S. Application Data

(63) Continuation of application No. 10/866,601, filed on Jun. 10, 2004.

(60) Provisional application No. 60/478,576, filed on Jun. 13, 2003.

(51) Int. Cl.
*A61N 1/18* (2006.01)

(52) U.S. Cl. .................. 607/3; 607/1; 607/2; 607/9; 607/119

(58) Field of Classification Search ............. 607/1–2, 607/9, 116, 119
See application file for complete search history.

(56) References Cited

U.S. PATENT DOCUMENTS

| | | | |
|---|---|---|---|
| 5,562,595 | A | 10/1996 | Neisz |
| 5,578,061 | A | 11/1996 | Stroetmann et al. |
| 5,916,239 | A | 6/1999 | Geddes et al. |
| 6,266,564 | B1 | 7/2001 | Hill et al. |
| 6,473,644 | B1 | 10/2002 | Terry et al. |
| 6,477,406 | B1 | 11/2002 | Turcott |
| 6,622,041 | B2 * | 9/2003 | Terry et al. ............ 607/9 |
| 6,684,105 | B2 | 1/2004 | Cohen et al. |
| 6,885,888 | B2 | 4/2005 | Rezai et al. |
| 6,907,293 | B2 | 6/2005 | Grill et al. |

(Continued)

OTHER PUBLICATIONS

Armour, J.A. et al. eds., (1994) *Neurocardiology*, Oxford University Press, 60-64.

(Continued)

*Primary Examiner*—Carl H Layno
*Assistant Examiner*—Deborah Malamud
(74) *Attorney, Agent, or Firm*—John P. White; Cooper & Dunham LLP

(57) ABSTRACT

A method is provided for treating a subject, including applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject. The method also includes configuring the current so as to treat a condition of the subject selected from the list consisting of: an autoimmune disease, an autoimmune inflammatory disease, multiple sclerosis, encephalitis, myelitis, immune-mediated neuropathy, myositis, dermatomyositis, polymyositis, inclusion body myositis, inflammatory demyelinating polyradiculoneuropathy, Guillain Barre syndrome, myasthenia gravis, inflammation of the nervous system, inflammatory bowel disease, Crohn's disease, ulcerative colitis, SLE (systemic lupus erythematosus), rheumatoid arthritis, vasculitis, polyarteritis nodosa, Sjogren syndrome, mixed connective tissue disease, glomerulonephritis, thyroid autoimmune disease, sepsis, meningitis, a bacterial infection, a viral infection, a fungal infection, sarcoidosis, hepatitis, and portal vein hypertension.

11 Claims, 8 Drawing Sheets

U.S. PATENT DOCUMENTS

| | | | |
|---|---|---|---|
| 7,136,700 | B1 | 11/2006 | Province |
| 7,509,166 | B2 | 3/2009 | Libbus et al. |
| 2003/0040774 | A1 | 2/2003 | Terry et al. |
| 2003/0045909 | A1 | 3/2003 | Gross et al. |
| 2004/0138721 | A1 | 7/2004 | Osorio et al. |

OTHER PUBLICATIONS

Baratta, R. et al., (1989) "Orderly stimulation of skeletal muscle motor units with tripolar nerve cuff electrode," *IEEE Transactions on Biomedical Engineering*, 36(1): 836-843.

Billette, J. et al., (1975) "Roles of the AV junction in determining the ventricular response to atrial fibrillation," *Can. J. Physiol. Pharmacol.*, 53(4): 575-585.

Borovikova, L.V. et al., (2000) "Vagus nerve stimulation attenuates the systemic inflammatory response to endotoxin," *Nature*, 405(6785): 458-462.

De Ferrari, G.M., (1991) "Vagal reflexes and survival during acute myocardial ischemia in conscious dogs with healed myocardial infarction," *Am. J. Physiol.*, 261(1 Pt 2): H63-H69.

Deurloo, K.E. et al., (1998) "Transverse tripolar stimulation of peripheral nerve: a modeling study of spatial selectivity," *Med. Bio. Eng. Comput.*, 36: 66-74.

Feliciano, L. et al., (1998) "Vagal nerve stimulation during muscarinic and beta-adrenergic blockade causes significant coronary artery dilation," *Cardiovasc. Res.*, 40(1): 45-55.

Fitzpatrick, D.M. et al., (1991) "A nerve cuff design for the selective activation and blocking of myelinated nerve fibers," *Ann. Intl. Conf. of the IEEE En g. in Med. and Bio.*, 13(2): 906-907.

Garrigue, S. et al., (1998) "Post-ganglionic vagal stimulation of the atrioventricular node reduces ventricular rate during atrial fibrillation," *Pacing and Clinical Electrophysiology*, 21(4), Part II, 878.

Goodall, E.V. et al., (1996) "Position-selective activation of peripheral nerve fibers with a cuff electrode," *IEEE Transactions on Biomedical Engineering*, 43(8): 851-856.

Grill, W.M. et al., (1997) "Inversion of the current-distance relationship by transient depolarization," *IEEE Transactions on Biomedical Engineering*, 44(1): 1-9.

Hayashi, H. et al., (1998) "Different effects of class Ic and III antiarrhythmic drugs on vagotonic atrial fibrillation the canine heart," *Journal of Cardiovascular Pharmacology*, 31: 101-107.

Higgins, C.B., (1973) "Parasympathetic control of the heart," *Pharmacol Rev.*, 25: 119-155.

Kwan, H. et al., (2001) "Cardiovascular adverse drug reactions during initiation of antiarrhythmic therapy for atrial fibrillation," *Canadian Journal of Hospital Pharmacists*, 54(1): 10-14.

Li, D. et al., (1999) "Promotion of atrial fibrillation by heart failure in dogs. Atrial remodeling of a different sort," *Circulation*, 100(1): 87-95.

Martin, P.J. et al., (1983) "Phasic effects of repetitive vagal stimulation on atrial contraction," *Circulation Research*: 52(6): 657-663.

Morady, F. et al., (1990) "Effects of resting vagal tone on accessory atrioventricular connections," *Circulation*: 81(1): 86-90.

Mushawar, V.K. et al., (2000) "Muscle recruitment through electrical stimulation of the lumbo-sacral spinal cord," *IEEE Transactions on Biomedical Engineering*, 8(1): 22-29.

Naples, G.G. et al., (1988) "A spiral nerve cuff electrode for peripheral nerve stimulation," *IEEE Transactions on Biomedical Engineering*, 35(11): 905-916.

Randall, W.C., ed., (1 977) *Neural Regulation of the Heart*, Oxford University Press, 100-106.

Rattay, F., (1989) "Analysis of models for extracellular fiber stimulation," *IEEE Transactions on Biomedical Engineering*, 36(2): 676-682.

Rijkhoff, N.J. et al., (1994) "Acute animal studies on the use of anodal block to reduce urethral resistance in sacral ro ot stimulation," *IEEE Transactions on Rehabilitation Engineering*, 2(2): 92-99.

Rijkhoff, N.J. et al., (1998) "Orderly recruitment of motoneurons in an acute rabbit model," *Proc. of the Annual Conf. of the IEEE Engineering in Medicine and Biology Society*, 20(5): 2564-2565.

Stramba-Badiale, M. et al., (1991) "Sympathetic-parasympathetic interaction and accentuated antagonism in conscious dogs," *American Journal of Physiology*, 260: H335-H340.

Sweeney, J.D. et al., (1990) "An asymmetric two electrode cuff for generation of unidirectionally propagated action potentials," *IEEE Transactions on Biomedical Engineering*, BME-33(6): 541-549.

Sweeney, J.D. et al., (1986) "A nerve cuff technique for selective excitation of peripheral nerve trunk regions," *IEEE Transactions on Biomedical Engineering*, 37(7): 706-715.

Takei, M. et al., (2001) "Vagal stimulation prior to atrial rapid pacing protects the atrium from electrical remodeling in anesthetized dogs," *Jpn. Circ. J.*, 65(12): 1077-1081.

Tarver, W.B. et al., (1992) "Clinical experience with a helical bipolar stimulating lead," *Pace*: vol. 15, Oct., Part II: 1545-1556.

Ungar, I.J. et al., (1986) "Generation of unidirectionally propagating action potentials using a monopolar electrode cuff," *Annals of Biomedical Engineering*, 14: 437-450.

Van Den Honert, C. et al., (1981) "A technique for collision block of peripheral nerve: Frequency dependence," *MP-12, IEEE Transactions on Biomedical Engineering*: 28: 379-382.

Vanoli, E. et al., (1991) "Vagal stimulation and prevention of sudden death in conscious dogs with a healed myocardial infarction," *Circulation Research*, 65(2): 1471-1481.

Veraart, C. et al., (1993) "Selective control of muscle activation with a multipolar nerve cuff electrode," *IEEE Transactions on Biomedical Engineering*, 40(7): 640-653.

Wang, H. et al., (2003) "Nicotinic acetylcholine receptor alpha-7 subunit is an essential regulator of inflammation," *Nature*, 421: 384-388.

Waninger, M.S. et al., (2000) "Electrophysiological control of ventricular rate during atrial fibrillation," *Pacing and Clinical Physiology*, 23(8): 1239-44.

Wijffels, M.C. et al., (1995) "Atrial fibrillation begets atrial fibrillation," *Circulation*, 92: 1954-1968.

Wijffels, M.C. et al., (1997) "Electrical remodeling due to atrial fibrillation in chronically instrumented conscious goats: roles of heurohumoral changes, ischemia, atrial stretch, and high rate of electrical activation," *Circulation*, 96(10): 3710-3720.

Jones, James F.X. et al., (1998) "Activity of C fibre cardiac vagal efferents in anaesthetized cats and rats," *Journal of Physiology*, vol. 507.3: 869-880.

Jones, James F.X. et al., (1995) "Heart rate responses to selective stimulation of cardiac vagal C fibres in anaesthetized cats, rats and rabbits," *Journal of Physiology*, vol. 489.1: 203-214.

Office Action issued Apr. 5, 2007 during the prosecution of Applicants' U.S. Appl. No. 10/488,334.

Van den Honert, C. et al., (1979) "Generation of unidirectionally propagated action potentials in a peripheral nerve by brief stimuli," *Science*, vol. 206: 1311-1312.

Office Action issued Apr. 1, 2009 during the prosecution of Applicants' U.S. Appl. No. 11/359,266.

Office Action issued Jun. 15, 2009 during the prosecution of Applicants' U.S. Appl. No. 11/064,446.

Office Action issued Jun. 23, 2009 during the prosecution of Applicants' U.S. Appl. No. 11/724,899.

Office Action issued Jun. 24, 2009 during the prosecution of Applicants' U.S. Appl. No. 11/978,379.

Office Action issued Jul. 21, 2009 during the prosecution of Applicants' U.S. Appl. No. 11/070,842.

Office Action issued Aug. 6, 2009 during the prosecution of Applicants' U.S. Appl. No. 10/205,475.

Office Action issued Aug. 21, 2009 during the prosecution of Applicants' U.S. Appl. No. 11/975,240.

Office Action issued Aug. 25, 2009 during the prosecution of Applicants' U.S. Appl. No. 11/975,241.

Morillo, C.A. et al., (Mar. 1, 1995) "Chronic Rapid Atrial Pacing. Structural, functional, and electrophysiological characteristics of a new model of sustained atrial fibrillation," *Circulation*: 91(5): 1588-1595.

\* cited by examiner

COMBINED PARASYMPATHETIC STIMULATION AND DRUG THERAPY

CROSS-REFERENCES TO RELATED APPLICATIONS

This application is a continuation of U.S. Ser. No. 10/866,601, filed Jun. 10, 2004, which claims benefit from U.S. Provisional Application No. 60/478,576, filed Jun. 13, 2003, and claims priority of PCT International Application No. PCT/IL2004/000495, filed Jun. 10, 2004, which designates the United States of America, the content of each of which is hereby incorporated herein by reference into this application.

FIELD OF THE INVENTION

The present invention relates generally to treating patients by application of electrical signals to selected tissue, and specifically to methods and apparatus for stimulating tissue for treating patients suffering from conditions such as atrial fibrillation, heart failure, or hypertension.

BACKGROUND OF THE INVENTION

The use of nerve stimulation for treating and controlling a variety of medical, psychiatric, and neurological disorders has seen significant growth over the last several decades, including for treatment of heart conditions. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic stimulation from the right and left vagus nerves. Low vagal nerve activity is considered to be related to various arrhythmias, including tachycardia, ventricular accelerated rhythm, and rapid atrial fibrillation. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Stimulation of the vagus nerve has been proposed as a method for treating various heart conditions, including atrial fibrillation and heart failure. Atrial fibrillation is a condition in which the atria of the heart fail to continuously contract in synchrony with the ventricles of the heart. During fibrillation, the atria undergo rapid and unorganized electrical depolarization, so that no contractile force is produced. The ventricles, which normally receive contraction signals from the atria (through the atrioventricular (AV) node), are inundated with signals, typically resulting in a rapid and irregular ventricular rate. Because of this rapid and irregular rate, the patient suffers from reduced cardiac output and/or a feeling of palpitations.

Current therapy for atrial fibrillation includes cardioversion and rate control. Cardioversion is the conversion of the abnormal atrial rhythm into normal sinus rhythm. This conversion is generally achieved pharmacologically or electrically. Rate control therapy is used to control the ventricular rate, while allowing the atria to continue fibrillation. This is generally achieved by slowing the conduction of signals through the AV node from the atria to the ventricles.

After cardioversion has been successfully performed, drug therapy is sometimes indicated for sinus rhythm maintenance or ventricular rate control (see Fuster et al., in their articles cited hereinbelow). Commonly used antiarrhythmic drugs for prophylactic maintenance of sinus rhythm include beta-blockers, amiodarone, disopyramide, dofetilide, flecainide, procainamide, propafenone, quinidine, and sotalol. Potential adverse effects of these drugs include hypotension, bradycardia, QT prolongation, ventricular proarrhythmia (ventricular tachycardia, including torsades de pointes), postural hypotension, and GI complaints, such as diarrhea. For ventricular rate control, commonly used drugs include beta-blockers (e.g., esmolol), calcium channel antagonists (e.g., verapamil, diltiazem) and digoxin. Potential adverse effects of these drugs include hypotension, heart block, heart failure, and bradycardia.

Bilgutay et al., in "Vagal tuning: a new concept in the treatment of supraventricular arrhythmias, angina pectoris, and heart failure," J. Thoracic Cardiovas. Surg. 56 (1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats. The authors further studied the use of the implanted device in conjunction with the administration of Isuprel, a sympathomimetic drug. They found that Isuprel retained its inotropic effect of increasing contractility, while its chronotropic effect was controlled by the vagal stimulation: "An increased end diastolic volume brought about by slowing of the heart rate by vagal tuning, coupled with increased contractility of the heart induced by the inotropic effect of Isuprel, appeared to increase the efficiency of cardiac performance" (p. 79).

An article by Moreira et al., entitled, "Chronic rapid atrial pacing to maintain atrial fibrillation: Use to permit control of ventricular rate in order to treat tachycardia induced cardiomyopathy," Pacing Clin Electrophysiol, 12(5):761-775 (May 1989), which is incorporated herein by reference, describes the acute induction of atrial fibrillation with rapid atrial pacing, and an associated reduction in ventricular rate with digitalis therapy. Different treatment protocols are described to induce and maintain atrial fibrillation, in order to bring a patient with NYHA class III-IV congestive heart failure to a more moderate NYHA class II.

An article by Preston et al., entitled, "Permanent rapid atrial pacing to control supraventricular tachycardia," Pacing Clin Electrophysiol, 2(3):331-334 (May 1979), which is incorporated herein by reference, describes a patient who had continuous supraventricular tachycardia with a ventricular rate of about 170. The arrhythmia was refractory to drugs and DC countershock, and did not convert with atrial pacing. Rapid atrial stimulation (pacing at 300-400/min) controlled the ventricular rate by simulating atrial fibrillation. This therapy was used on a permanent basis for more than five months.

U.S. Pat. No. 6,473,644 to Terry, Jr. et al., which is incorporated herein by reference, describes a method for treating patients suffering from heart failure to increase cardiac output, by stimulating or modulating the vagus nerve with a sequence of substantially equally-spaced pulses by an implanted neurostimulator. The frequency of the stimulating pulses is adjusted until the patient's heart rate reaches a target rate within a relatively stable target rate range below the low end of the patient's customary resting heart rate.

US Patent Application Publication 2003/0040774 to Terry et al., which is incorporated herein by reference, describes a device for treating patients suffering from congestive heart failure. The device includes an implantable neurostimulator for stimulating the patient's vagus nerve at or above the cardiac branch with an electrical pulse waveform at a stimulating rate sufficient to maintain the patient's heart beat at a rate well below the patient's normal resting heart rate, thereby allowing rest and recovery of the heart muscle, to increase in coronary blood flow, and/or growth of coronary capillaries. A metabolic need sensor detects the patient's current physical state and concomitantly supplies a control signal to the neurostimulator to vary the stimulating rate. If the detection indicates a state of rest, the neurostimulator rate reduces the patient's heart rate below the patient's normal resting rate. If the detection indicates physical exertion, the neurostimulator rate increases the patient's heart rate above the normal resting rate.

US Patent Publication 2003/0045909 to Gross et al., which is assigned to the assignee of the present patent application and is incorporated herein by reference, describes apparatus for treating a heart condition of a subject, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

The following articles and book, which are incorporated herein by reference, may be of interest:

Levy M N et al., in "Parasympathetic Control of the Heart," Nervous Control of Vascular Function, Randall W C ed., Oxford University Press (1984)

Levy M N et al. ed., Vagal Control of the Heart: Experimental Basis and Clinical Implications (The Bakken Research Center Series Volume 7), Futura Publishing Company, Inc., Armonk, N.Y. (1993)

Randall W C ed., Neural Regulation of the Heart, Oxford University Press (1977), particularly pages 100-106.

Armour J A et al. eds., Neurocardiology, Oxford University Press (1994)

Perez M G et al., "Effect of stimulating non-myelinated vagal axon on atrio-ventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," Am J Physiol 237(3):H275-81 (1979)

Fuster V and Ryden L E et al., "ACC/AHA/ESC Practice Guidelines—Executive Summary," J Am Coll Cardiol 38(4): 1231-65 (2001)

Fuster V and Ryden L E et al., "ACC/AHA/ESC Practice Guidelines—Full Text," J Am Coll Cardiol 38(4):1266i-1266lxx (2001)

Morady F et al., "Effects of resting vagal tone on accessory atrioventricular connections," Circulation 81(1):86-90 (1990)

Waninger M S et al., "Electrophysiological control of ventricular rate during atrial fibrillation," PACE 23:1239-1244 (2000)

Wijffels M C et al., "Electrical remodeling due to atrial fibrillation in chronically instrumented conscious goats: roles of neurohumoral changes, ischemia, atrial stretch, and high rate of electrical activation," Circulation 96(10):3710-20 (1997)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Lew S J et al., "Stroke prevention in elderly patients with atrial fibrillation," Singapore Med J 43(4):198-201 (2002)

Higgins C B, "Parasympathetic control of the heart," Pharmacol. Rev. 25:120-155 (1973)

Hunt R, "Experiments on the relations of the inhibitory to the accelerator nerves of the heart," J. Exptl. Med. 2:151-179 (1897)

Billette J et al., "Roles of the AV junction in determining the ventricular response to atrial fibrillation," Can J Physiol Pharamacol 53(4)575-85 (1975)

Stramba-Badiale M et al., "Sympathetic-Parasympathetic Interaction and Accentuated Antagonism in Conscious Dogs," American Journal of Physiology 260 (2Pt 2):H335-340 (1991)

Garrigue S et al., "Post-ganglionic vagal stimulation of the atrioventricular node reduces ventricular rate during atrial fibrillation," PACE 21(4), 878 (Part II) (1998)

Kwan H et al., "Cardiovascular adverse drug reactions during initiation of antiarrhythmic therapy for atrial fibrillation," Can J Hosp Pharm 54:10-14 (2001)

Jidéus L, "Atrial fibrillation after coronary artery bypass surgery: A study of causes and risk factors," Acta Universitatis Upsaliensis, Uppsala, Sweden (2001)

Borovikova L V et al., "Vagus nerve stimulation attenuates the systemic inflammatory response to endotoxin," Nature 405(6785):458-62 (2000)

Wang H et al., "Nicotinic acetylcholine receptor alpha-7 subunit is an essential regulator of inflammation," Nature 421:384-388 (2003)

Vanoli E et al., "Vagal stimulation and prevention of sudden death in conscious dogs with a healed myocardial infarction," Circ Res 68(5):1471-81 (1991)

De Ferrari G M, "Vagal reflexes and survival during acute myocardial ischemia in conscious dogs with healed myocardial infarction," Am J Physiol 261(1 Pt 2):H63-9 (1991)

Li D et al., "Promotion of Atrial Fibrillation by Heart Failure in Dogs: Atrial Remodeling of a Different Sort," Circulation 100(1):87-95 (1999)

Feliciano L et al., "Vagal nerve stimulation during muscarinic and beta-adrenergic blockade causes significant coronary artery dilation," Cardiovasc Res 40(1):45-55 (1998)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

U.S. Pat. No. 5,330,507 to Schwartz, which is incorporated herein by reference, describes a cardiac pacemaker for preventing or interrupting tachyarrhythmias and for applying pacing therapies to maintain the heart rhythm of a patient within acceptable limits. The device automatically stimulates the right or left vagus nerves as well as the cardiac tissue in a concerted fashion dependent upon need. Continuous and/or phasic electrical pulses are applied. Phasic pulses are applied in a specific relationship with the R-wave of the ECG of the patient.

European Patent Application EP 0 688 577 to Holmström et al., which is incorporated herein by reference, describes a device to treat atrial tachyarrhythmia by detecting arrhythmia and stimulating a parasympathetic nerve that innervates the heart, such as the vagus nerve.

U.S. Pat. Nos. 5,690,681 and 5,916,239 to Geddes et al., which are incorporated herein by reference, describe closed-loop, variable-frequency, vagal-stimulation apparatus for control of ventricular rate during atrial fibrillation. The apparatus stimulates the left vagus nerve, and automatically and continuously adjusts the vagal stimulation frequency as a function of the difference between actual and desired ventricular excitation rates. In an alternative embodiment, the apparatus automatically adjusts the vagal stimulation frequency as a function of the difference between ventricular excitation rate and arterial pulse rate in order to eliminate or minimize pulse deficit.

US Patent Publication 2003/0229380 to Adams et al., which is incorporated herein by reference, describes techniques for electrically stimulating the right vagus nerve in order to reduce the heart rate of a patient suffering from conditions such as chronic heart failure, ischemia, or acute myocardial infarction. The amount of energy of the stimulation may be determined in accordance with a difference between the patient's actual heart rate and a maximum target heart rate for the patient. Delivery of energy is preferably synchronized with the detection of a P-wave. Automatic adjustment of the target heart rate may be based on current day and/or time of day information, and patient physical activity. The voltage, pulse width, or number of pulses in the stimulation may be controlled.

U.S. Pat. No. 5,203,326 to Collins, which is incorporated herein by reference, describes a pacemaker which detects a cardiac abnormality and responds with electrical stimulation of the heart combined with vagus nerve stimulation. The vagal stimulation frequency is progressively increased in one-minute intervals, and, for the pulse delivery rate selected, the heart rate is described as being slowed to a desired, stable level by increasing the pulse current.

U.S. Pat. No. 6,511,500 to Rahme, which is incorporated herein by reference, describes various aspects of the effects of autonomic nervous system tone on atrial arrhythmias, and its interaction with class III antiarrhythmic drug effects. The significance of sympathetic and parasympathetic activation are described as being evaluated by determining the effects of autonomic nervous system using vagal and stellar ganglions stimulation, and by using autonomic nervous system neurotransmitters infusion (norepinephrine, acetylcholine).

U.S. Pat. No. 5,199,428 to Obel et al., which is incorporated herein by reference, describes a cardiac pacemaker for detecting and treating myocardial ischemia. The device automatically stimulates the vagal nervous system as well as the cardiac tissue in a concerted fashion in order to decrease cardiac workload and thereby protect the myocardium.

U.S. Pat. Nos. 5,334,221 to Bardy and 5,356,425 to Bardy et al., which are incorporated herein by reference, describe a stimulator for applying stimulus pulses to the AV nodal fat pad in response to the heart rate exceeding a predetermined rate, in order to reduce the ventricular rate. The device also includes a cardiac pacemaker which serves to pace the ventricle in the event that the ventricular rate is lowered below a pacing rate, and provides for feedback control of the stimulus parameters applied to the AV nodal fat pad, as a function of the determined effect of the stimulus pulses on the heart rate.

U.S. Pat. No. 5,522,854 to Ideker et al., which is incorporated herein by reference, describes techniques for preventing arrhythmia by detecting a high risk of arrhythmia and then stimulating afferent nerves to prevent the arrhythmia.

U.S. Pat. No. 6,434,424 to Igel et al., which is incorporated herein by reference, describes a pacing system with a mode switching feature and ventricular rate regularization function adapted to stabilize or regularize ventricular heart rate during chronic or paroxysmal atrial tachyarrhythmia.

US Patent Application Publication 2002/0120304 to Mest, which is incorporated herein by reference, describes a method for regulating the heart rate of a patient by inserting into a blood vessel of the patient a catheter having an electrode at its distal end, and directing the catheter to an intravascular location so that the electrode is adjacent to a selected cardiac sympathetic or parasympathetic nerve.

U.S. Pat. Nos. 6,006,134 and 6,266,564 to Hill et al., which are incorporated herein by reference, describe an electrostimulation device including a pair of electrodes for connection to at least one location in the body that affects or regulates the heartbeat.

PCT Publication WO 02/085448 to Foreman et al., which is incorporated herein by reference, describes a method for protecting cardiac function and reducing the impact of ischemia on the heart, by electrically stimulating a neural structure capable of carrying the predetermined electrical signal from the neural structure to the "intrinsic cardiac nervous system," which is defined and described therein.

U.S. Pat. No. 5,243,980 to Mehra, which is incorporated herein by reference, describes techniques for discrimination between ventricular and supraventricular tachycardia. In response to the detection of the occurrence of a tachycardia, stimulus pulses are delivered to one or both of the SA and AV nodal fat pads. The response of the heart rhythm to these stimulus pulses is monitored. Depending upon the change or lack of change in the heart rhythm, a diagnosis is made as to the origin of the tachycardia.

U.S. Pat. No. 5,658,318 to Stroetmann et al., which is incorporated herein by reference, describes a device for detecting a state of imminent cardiac arrhythmia in response to activity in nerve signals conveying information from the autonomic nerve system to the heart. The device comprises a sensor adapted to be placed in an extracardiac position and to detect activity in at least one of the sympathetic and vagus nerves.

U.S. Pat. No. 6,292,695 to Webster, Jr. et al., which is incorporated herein by reference, describes a method for controlling cardiac fibrillation, tachycardia, or cardiac arrhythmia by the use of a catheter comprising a stimulating electrode, which is placed at an intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

U.S. Pat. No. 6,134,470 to Hartlaub, which is incorporated herein by reference, describes an implantable anti-arrhythmia system which includes a spinal cord stimulator coupled to an implantable heart rhythm monitor. The monitor is adapted to detect the occurrence of tachyarrhythmias or of precursors thereto and, in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation.

A number of patents and articles describe other methods and devices for stimulating nerves to achieve a desired effect. Often these techniques include a design for an electrode or electrode cuff.

US Patent Publication 2003/0050677 to Gross et al., which is assigned to the assignee of the present patent application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

U.S. Pat. Nos. 4,608,985 to Crish et al. and 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode. The current applied to the electrodes blocks nerve transmission, but, as described, does not activate the nerve fibers in either direction.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33 (6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Manfredi M, "Differential block of conduction of larger fibers in peripheral nerve by direct current," Arch. Ital. Biol., 108:52-71 (1970)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j,$$

where U is the potential, σ is the conductance tensor specifying the conductance of the various materials (electrode housing, axon, intracellular fluid, etc.), and j is a scalar function representing the current source density specifying the locations of current injection.

U.S. Pat. No. 5,231,988 to Wernicke et al., which is incorporated herein by reference, describes techniques for treating and controlling diabetes and other systemic pancreatic endocrine disorders attributable to abnormal levels of secretion of endogenous insulin. An electrical stimulator implanted into or worn external to the patient's body is adapted, when activated, to generate a programmable electrical waveform for application to electrodes implanted on the vagus nerve of the patient. The electrical waveform is programmed using parameter values selected to stimulate or inhibit the vagus nerve to modulate the electrical activity thereof to increase or decrease secretion of natural insulin by the patient's pancreas. The stimulator is selectively activated manually by the patient in response to direct measurement of blood glucose or symptoms, or is activated automatically by programming the activation to occur at predetermined times and for predetermined intervals during the circadian cycle of the patient. Alternatively, the automatic activation is achieved using an implanted sensor to detect the blood glucose concentration, and is triggered when the patient's blood glucose concentration exceeds or falls below a predetermined level depending on whether diabetes or hypoglycemia is being treated.

SUMMARY OF THE INVENTION

In some embodiments of the present invention, a method for enhancing or sustaining the efficacy of drug treatment for atrial fibrillation (AF) comprises administering a drug to a patient and applying signals to a vagus nerve that innervates the heart of the patient. The drug administered typically includes a sinus rhythm maintenance drug (i.e., an antiarrhythmic drug) or a ventricular rate control drug. The efficacy of the drug is typically enhanced or sustained by (a) configuring the signals so as to prevent electrical remodeling of the atria, which remodeling generally reduces drug effectiveness over time, and/or (b) configuring the signals so as to achieve a therapeutic benefit similar to that of the drug, which typically results in a synergistic effect between the therapeutic benefit of the drug and the vagal stimulation. For enhancing the effectiveness of antiarrhythmic drugs, the signals are typically configured to increase vagal tone, produce rhythmic vagal activity, and/or reduce the atrial effective refractory period (AERP). The effectiveness of ventricular rate control drugs is typically enhanced by applying vagal stimulation to control ventricular response rate and/or to improve cardiac output.

In some embodiments of the present invention, a method for enhancing or sustaining the efficacy of drug treatment for AF comprises administering a drug to the patient, applying signals to the vagus nerve, and configuring the signals to reduce the mechanical tension on at least one atrium of the subject. Such reduced mechanical tension generally reduces the risk of AF. For some applications, such vagal stimulation is applied without administering the drug.

In some embodiments of the present invention, the safety of a drug administered to the patient is improved by applying signals to the vagus nerve, and configuring the signals so as to prevent adverse effects sometimes caused by the drug, such as repolarization abnormalities (e.g., prolongation of the QT interval), bradycardia, and/or ventricular tachyarrhythmia (e.g., ventricular fibrillation). In some cases, the drug can safely be administered to patients who otherwise could not tolerate the drug because of such adverse effects. In addition, in some cases, adverse effects of the drug are prevented or diminished by allowing the use of lower dosages of the drug by enhancing or sustaining the efficacy of the drug, as described above.

In some embodiments of the present invention, a method for enhancing or sustaining the efficacy of drug treatment for heart failure comprises administering a drug to a patient and applying signals to a vagus nerve that innervates the heart of the patient. The signals are configured so as to treat the heart failure, which typically results in a synergistic effect between the therapeutic benefit of the drug and the vagal stimulation. Alternatively or additionally, the signals are configured so as to prevent adverse effects sometimes caused by the drug, such as ventricular arrhythmia, idioventricular arrhythmia, premature ventricular contractions, and/or ventricular tachycardia. In addition, in some cases, adverse effects of the drug are prevented or diminished by allowing the use of lower dosages of the drug because of the synergistic effect of the vagal stimulation with the drug treatment.

In some embodiments of the present invention, a method for increasing vagal tone comprises applying signals to the vagus nerve, and configuring the signals to stimulate the vagus nerve, thereby delivering parasympathetic nerve stimulation to the heart, while at the same time minimizing the heart-rate-lowering effects of the stimulation. Such treatment generally results in the beneficial effects of vagal stimulation in clinical situations in which heart rate reduction is not indicated or is contraindicated. For example, such treatment is typically appropriate for heart failure patients who suffer from bradycardia when taking beta-blockers. In addition, such treatment is believed by the inventors to reduce the risk of sudden cardiac death in some patients.

In some embodiments of the present invention, a method for preventing or reducing fibrosis and/or inflammation of the heart comprises applying signals to a vagus nerve that innervates the heart of the patient. Substantially continuous application of such stimulation generally modulates immune system responses, thereby reducing atrial, ventricular, and/or coronary inflammation and/or fibrosis. For some applications, such stimulation is applied for more than about three weeks. Conditions that are believed to be at least partially immune-modulated, and therefore to generally benefit from such vagal stimulation, include, but are not limited to, atrial and ventricular remodeling (e.g., induced by AF, heart failure, myocarditis, and/or myocardial infarct), restenosis, and atherosclerosis.

In some embodiments of the present invention, signals are applied to a vagus nerve of a patient, and the signals are configured to inhibit propagation of naturally-generated efferent action potentials in the vagus nerve. It is hypothesized by the inventors that such inhibition is useful for treating AF, typically by enhancing drug efficacy, and for preventing bradycardia.

In some embodiments of the present invention, electrical signals are applied, typically on a long-term basis, to a vagus nerve of a subject not necessarily suffering from a heart condition, in order to increase the life expectancy, quality of life, and/or healthiness of the subject. Such signals are typically configured to not reduce the heart rate below normal range for a typical human. Such chronic vagal stimulation is hypothesized by the inventors to be effective for increasing life expectancy, quality of life, and/or healthiness by (a) causing a reduction in or prevention of cardiovascular disease and/or events, (b) having an anti-inflammatory effect in the heart or in the rest of the body, (c) reducing the average heart rate, (d) reducing metabolic rate, and/or (e) generally having an anti-stress effect.

In some embodiments of the present invention, apparatus is provided for applying the signals to the vagus nerve, comprising an electrode device and a control unit. The electrode device is applied to a portion of the vagus nerve that innervates the heart of the patient. The control unit drives the electrode device to apply signals to the vagus nerve, and configures the signals based on the desired therapeutic effect, as described above.

In some embodiments of the present invention, when applying the signals to the vagus nerve, the control unit drives the electrode device to (a) apply signals to induce the propagation of efferent action potentials towards the heart, and (b) suppress artificially-induced afferent action potentials towards the brain, in order to minimize any unintended side effect of the signal application. When inducing efferent action potentials towards the heart, the control unit typically drives the electrode device to selectively recruit nerve fibers beginning with smaller-diameter fibers, and to recruit progressively larger-diameter fibers as the desired stimulation level increases. Typically, in order to achieve this smaller-to-larger diameter fiber recruitment order, the control unit stimulates fibers essentially of all diameters using cathodic current from a central cathode, while simultaneously inhibiting fibers in a larger-to-smaller diameter order using anodal current ("efferent anodal current") from a set of one or more anodes placed between the central cathode and the edge of the electrode device closer to the heart ("the efferent anode set"). Thus, for example, if a small anodal current is applied, then action potentials induced by the cathodic current in the larger diameter fibers are inhibited (because the larger diameter fibers are sensitive to even a small anodal current), while action potentials induced by the cathodic current in smaller fibers are allowed to propagate towards the heart. The amount of parasympathetic stimulation delivered to the heart may generally be increased by decreasing the number of fibers affected by the efferent anodal current, in a smaller-to-larger diameter order, e.g., by decreasing the amplitude or frequency of the efferent anodal current applied to the nerve. Alternatively, the cathodic current is increased in order to increase the parasympathetic stimulation.

The control unit typically suppresses afferent action potentials induced by the cathodic current by inhibiting essentially all or a large fraction of fibers using anodal current ("afferent anodal current") from a second set of one or more anodes (the "afferent anode set"). The afferent anode set is typically placed between the central cathode and the edge of the electrode device closer to the brain (the "afferent edge"), to block a large fraction of fibers from conveying signals in the direction of the brain during application of the afferent anodal current.

In some embodiments of the present invention, the cathodic current is applied with an amplitude sufficient to induce action potentials in large- and medium-diameter fibers (e.g., A- and B-fibers), but insufficient to induce action potentials in small-diameter fibers (e.g., C-fibers). Simultaneously, an anodal current is applied in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked, as described above. By not stimulating large-diameter fibers, such stimulation generally avoids adverse effects sometimes associated with recruitment of such large fibers, such as dyspnea and hoarseness. Stimulation of small-diameter fibers is avoided because these fibers transmit pain sensations and are important for regulation of reflexes such as respiratory reflexes.

In some embodiments of the present invention, the efferent anode set comprises a plurality of anodes. Application of the efferent anodal current in appropriate ratios from the plurality of anodes in these embodiments generally minimizes the "virtual cathode effect," whereby application of too large an anodal current creates a virtual cathode, which stimulates rather than blocks fibers. When such techniques are not used, the virtual cathode effect generally hinders blocking of smaller-diameter fibers, because a relatively large anodal current is typically necessary to block such fibers, and this same large anodal current induces the virtual cathode effect. Likewise, the afferent anode set typically comprises a plurality of anodes in order to minimize the virtual cathode effect in the direction of the brain.

In some embodiments of the present invention, vagal stimulation is applied in a series of pulses. The application of the series of pulses in each cardiac cycle typically commences after a variable delay after a detected R-wave, P-wave, or other feature of an ECG. For some applications, other parameters of the applied series of pulses are also varied in real time. Such other parameters include amplitude, number of pulses per trigger (PPT), pulse duration, and pulse repetition interval (i.e., the interval between the leading edges of two consecutive pulses). For some applications, the delay and/or one or more of the other parameters are calculated in real time using a function, the inputs of which include one or more preprogrammed but updateable constants and one or more sensed parameters, such as the R-R interval between cardiac cycles and/or the P-R interval. Alternatively or additionally, a lookup table of parameters, such as delays and/or other parameters, is used to determine in real time the appropriate parameters for each application of pulses, based on the one or more sensed parameters, and/or based on a predetermined sequence stored in the lookup table.

"Vagus nerve," and derivatives thereof, as used in the specification and the claims, is to be understood to include portions of the left vagus nerve, the right vagus nerve, and branches of the vagus nerve such as the superior cardiac nerve, superior cardiac branch, and inferior cardiac branch. Similarly, stimulation of the vagus nerve is described herein by way of illustration and not limitation, and it is to be understood that stimulation of other autonomic nerves, including nerves in the epicardial fat pads, a carotid artery, an internal jugular vein, a carotid sinus, a vena cava vein, and/or a pulmonary vein, for treatment of heart conditions or other conditions, is also included within the scope of the present invention.

There is therefore provided, in accordance with an embodiment of the present invention, a method for treating a subject suffering from atrial fibrillation (AF), including:

administering a drug for treating the AF to the subject;

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current to increase vagal tone of the subject, so as to treat the AF.

In an embodiment, configuring the current includes configuring the current so as to enhance an efficacy of the drug.

In an embodiment, the method includes detecting an occurrence of the AF, and applying the current includes applying the current responsive to the detecting of the occurrence.

In an embodiment, administering the drug includes administering the drug at a dosage determined independently of applying the current.

In an embodiment, administering the drug includes administering the drug at a dosage lower than a dosage determined independently of applying the current.

In an embodiment, the subject additionally suffers from heart failure (HF), and the method includes administering a HF drug for treating the HF of the subject, and configuring the current includes configuring the current so as to enhance an efficacy of the HF drug.

For some applications, configuring the current so as to enhance the efficacy of the drug includes configuring the current so as to prevent electrical remodeling of at least one atrium of the subject. Alternatively or additionally, configuring the current so as to enhance the efficacy of the drug includes configuring the current so as to delay electrical remodeling of at least one atrium of the subject.

In an embodiment, configuring the current so as to enhance the efficacy of the drug includes configuring the current so as to achieve a therapeutic effect similar to that of the drug.

In an embodiment, configuring the current so as to enhance the efficacy of the drug includes configuring the current so as to reduce a QT interval of an electrocardiogram (ECG) of the subject.

In an embodiment, administering the drug includes administering a beta-blocker.

In an embodiment, administering the drug includes administering a sinus rhythm maintenance drug. For some applications, configuring the current so as to enhance the efficacy of the drug includes configuring the current so as to increase vagal tone of the subject. For some applications, configuring the current so as to enhance the efficacy of the drug includes configuring the current so as to reduce an atrial effective refractory period of the subject. For some applications, configuring the current so as to enhance the efficacy of the drug includes configuring the current so as to have an antiarrhythmic effect on an atrium of the subject. For some applications, configuring the current so as to enhance the efficacy of the drug includes configuring the current to reduce mechanical tension on at least one atrium of the subject.

For some applications, administering the sinus rhythm maintenance drug includes administering a beta-blocker. Alternatively or additionally, administering the sinus rhythm maintenance drug includes administering quinidine. Further alternatively or additionally, administering the sinus rhythm maintenance drug includes administering a drug selected from the list consisting of: digoxin, amiodarone, disopyramide, dofetilide, a class IC drug, procainamide, and sotalol.

For some applications, the method includes applying conventional cardioversion to the subject so as to treat the AF. For some applications, configuring the current so as to enhance the efficacy of the drug includes configuring the current so as to induce rhythmic vagal activity in the subject.

In an embodiment, administering the drug includes administering a ventricular rate control drug. For some applications, configuring the current so as to enhance the efficacy of the drug includes configuring the current so as to control a ventricular response rate of the subject. For some applications, configuring the current so as to enhance the efficacy of the drug includes configuring the current so as to improve cardiac output of the subject.

For some applications, administering the ventricular rate control drug includes administering a beta-blocker. Alternatively or additionally, administering the ventricular rate control drug includes administering a drug selected from the list consisting of: a calcium channel antagonist and digoxin.

In an embodiment, administering the drug includes administering an antithrombotic drug. For some applications, administering the antithrombotic drug includes administering an anticoagulation drug that inhibits a coagulation cascade. Alternatively or additionally, administering the antithrombotic drug includes administering a drug that inhibits platelet aggregation. For some applications, configuring the current so as to enhance the efficacy of the antithrombotic drug includes configuring the current so as to increase atrial motion of the subject. For some applications, administering the antithrombotic drug includes selecting a dosage of the drug to achieve a target international normalized ratio (INR) lower than a target INR determined independently of applying the current. For some applications, configuring the current so as to enhance the efficacy of the drug includes configuring the current so as to induce rhythmic vagal activity in the subject.

There is also provided, in accordance with an embodiment of the present invention, a method for treating a subject suffering from heart failure (HF), including:

administering a drug for treating the HF to the subject;

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current so as to enhance an efficacy of the drug.

In an embodiment, configuring the current so as to enhance the efficacy of the drug includes configuring the current so as to treat the HF.

For some applications, configuring the current so as to enhance the efficacy of the drug includes configuring the current to inhibit propagation of naturally-generated efferent action potentials traveling through the site.

In an embodiment, administering the drug includes administering a positive inotropic drug. For some applications, administering the positive inotropic drug includes administering a positive inotropic drug selected from the list consisting of: digoxin, dopamine, dobutamine, adrenaline, amrinone, and milrinone.

In an embodiment, administering the drug includes administering a preload reduction drug. For some applications, administering the preload reduction drug includes administering a preload reduction drug selected from the list consisting of: an ACE inhibitor, a nitrate, and sodium nitroprusside. For some applications, configuring the current so as to enhance the efficacy of the preload reduction drug includes configuring the current so as to decrease atrial contractile force of a heart of the subject. For some applications, applying the current includes applying the current to the site intermittently during alternating "on" and "off" periods. For some applications, applying the current intermittently includes setting each of the "on" periods to have a duration of between about 1 and about 15 seconds, and each of the "off" periods to have a duration of between about 5 and about 20 seconds.

There is further provided, in accordance with an embodiment of the present invention, a method for treating a subject suffering from a condition, including:

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current to increase vagal tone of the subject, and to minimize an effect of the applying of the current on a heart rate of the subject, so as to treat the condition.

In an embodiment, the condition is selected from the list consisting of: atrial fibrillation, heart failure, atherosclerosis, restenosis, myocarditis, cardiomyopathy, post-myocardial infarct remodeling, and hypertension, and configuring the current includes configuring the current so as to treat the selected condition. Alternatively or additionally, the condition is selected from the list consisting of: obesity, constipation, irritable bowel syndrome, rheumatoid arthritis, glomerulonephritis, an autoimmune disease, multiple sclerosis, hepatitis, pancreatitis, portal vein hypertension, thyroiditis, type I diabetes, and type II diabetes, and configuring the current includes configuring the current so as to treat the selected condition.

For some applications, configuring the current includes configuring the current so as to reduce a risk of sudden cardiac death of the subject.

For some applications, applying the current includes applying the current substantially only at nighttime. For some applications, applying the current includes applying the current during a daytime period and during a nighttime period, the applying during the nighttime period being longer than the applying during the daytime period.

For some applications, applying the current includes detecting exercise by the subject, and applying the current responsively to the detecting.

For some applications, applying the current to the site of the subject includes selecting a subject that is receiving a heart-rate lowering drug, and who has achieved a heart rate within a desired range prior to initiation of applying the current.

For some applications, applying the current to the site of the subject includes selecting a subject who experiences, when the heart rate is reduced, a symptom selected from the list consisting of: discomfort, and a reduction in exercise capacity.

For some applications, applying the current to the site of the subject includes selecting a subject who has a tendency towards bradycardia when receiving vagal stimulation that is not configured to minimize an effect thereof on the heart rate.

For some applications, the condition includes low cardiac output, and configuring the current includes configuring the current so as to treat the low cardiac output. For some applications, the condition includes acute myocardial infarction with cardiogenic shock, and configuring the current includes configuring the current so as to treat the acute myocardial infarction. For some applications, the condition includes heart failure and beta-blocker-induced bradycardia, and configuring the current includes configuring the current so as to treat the heart failure and bradycardia.

In an embodiment, the method includes applying a pacing signal to a heart of the subject in conjunction with applying the current to the site.

In an embodiment, the method includes sensing a heart rate of the subject, and configuring the current includes configuring the current using a feedback loop, an input of which is the sensed heart rate.

There is still further provided, in accordance with an embodiment of the present invention, a method for treating a subject suffering from a condition, including:

administering to the subject a drug for treating the condition;

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current so as to reduce an adverse effect sometimes caused by the drug.

In an embodiment, the condition includes atrial fibrillation (AF), administering the drug includes administering a drug for treating the AF, and configuring the current includes configuring the current so as to reduce the adverse effect sometimes caused by the AF drug.

In an embodiment, the condition includes heart failure (HF), administering the drug includes administering a drug for treating the HF, and configuring the current includes configuring the current so as to reduce the adverse effect sometimes caused by the HF drug.

In an embodiment, the condition includes an emergency condition, and administering the drug includes administering atropine.

In an embodiment, the adverse effect includes idioventricular arrhythmia, and configuring the current includes configuring the current so as to reduce the idioventricular arrhythmia. In an embodiment, the adverse effect includes premature ventricular contractions, and configuring the current includes configuring the current so as to reduce the premature ventricular contractions. In an embodiment, the adverse effect includes ventricular tachycardia, and configuring the current includes configuring the current so as to reduce the ventricular tachycardia.

In an embodiment, the adverse effect includes ventricular arrhythmia, and configuring the current includes configuring the current so as to reduce the ventricular arrhythmia. For some applications, configuring the current includes configuring the current so as to induce rhythmic vagal activity in the subject.

In an embodiment, administering the drug includes administering the drug at a dosage lower than a usual dosage determined independently of applying the current, and configuring the current includes configuring the current so as to enhance an efficacy of the drug to a degree that the lower dosage has substantially the same efficacy as the usual dosage. For some applications, administering the drug includes administering digoxin at the lower dosage.

In an embodiment, the adverse effect includes ventricular tachyarrhythmia, and configuring the current includes configuring the current so as to reduce the ventricular tachyarrhythmia. For some applications, the ventricular tachyarrhythmia includes ventricular fibrillation, and configuring the current includes configuring the current so as to reduce the ventricular fibrillation. For some applications, administering the drug includes administering a drug selected from the list consisting of: an antiarrhythmic drug, and a positive inotropic drug.

In an embodiment, the adverse effect includes a repolarization abnormality, and configuring the current includes configuring the current so as to reduce the repolarization abnormality. For some applications, the repolarization abnormality includes a prolongation of a QT interval of the subject, and configuring the current includes configuring the current so as to reduce the prolongation of the QT interval.

In an embodiment, administering the drug includes administering the drug at a dosage greater than a dosage determined independently of applying the current, and configuring the current so as to reduce the adverse effect includes configuring the current so as to reduce an adverse effect sometimes caused by the greater dosage. For some applications, administering the drug includes administering a class IC drug.

In an embodiment, administering the drug includes administering a positive inotropic agent for a period of time having a duration greater than about one day. For some applications, administering the positive inotropic agent includes administering the positive inotropic agent for a period having a duration greater than about 7 days. For some applications, administering the positive inotropic agent includes administering a positive inotropic agent other than digitalis. For some applications, the adverse effect is selected from the list consisting of: a chronotropic effect of the positive inotropic agent, and a proarrhythmic effect of the positive inotropic agent, and configuring the current includes configuring the current so as to reduce the selected adverse effect. For some applications, the subject is in a stable condition, and administering the positive inotropic agent includes administering the positive inotropic agent to the stable subject.

In an embodiment, the adverse effect includes an occurrence of bradycardia, and configuring the current includes configuring the current so as to reduce the occurrence of bradycardia. For some applications, configuring the current includes configuring the current to inhibit propagation of naturally-generated efferent action potentials traveling through the site, so as to reduce the bradycardia. For some applications, applying the current includes detecting the occurrence of bradycardia, and terminating applying the current responsive to the detecting. For some applications, applying the current includes detecting the occurrence of bradycardia, and reducing an intensity of the current responsive to the detecting. For some applications, the method includes detecting the occurrence of bradycardia, and, responsive to the detecting, applying a pacing signal to a heart of the subject.

There is additionally provided, in accordance with an embodiment of the present invention, a method for treating a subject, including:

applying a current to a site of the subject selected from the list consisting of: a vagus nerve of the subject, and epicardial fat pad of the subject, a pulmonary vein of the subject, a carotid artery of the subject, a carotid sinus of the subject, a vena cava vein of the subject, and an internal jugular vein of the subject; and configuring the current so as to reduce a heart condition of the subject selected from the list consisting of: fibrosis of the heart, and inflammation of the heart.

For some applications, applying the current includes substantially continuously applying the current. For some applications, applying the current includes applying the current during an application period lasting at least about three weeks, and configuring the current such that, during the application period, a longest duration of time in which no current is applied is less than four hours. For some applications, applying the current includes applying the current for a period having a duration of more than about three weeks.

For some applications, the heart condition includes the fibrosis of the heart, and configuring the current includes configuring the current so as to reduce the fibrosis. Alternatively or additionally, the heart condition includes the inflammation of the heart, and configuring the current includes configuring the current so as to reduce the inflammation.

There is yet additionally provided, in accordance with an embodiment of the present invention, a method for treating a subject, including:

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current to inhibit propagation of naturally-generated efferent action potentials traveling through the site, while inhibiting no more than about 10% of naturally-generated afferent action potentials traveling through the site, so as to treat a condition of the subject.

In an embodiment, the condition includes atrial fibrillation (AF), and configuring the current includes configuring the current so as to treat the AF. In an embodiment, the condition includes bradycardia, and configuring the current includes configuring the current so as to prevent the bradycardia.

In an embodiment, the method includes administering to the subject a drug for treating the condition, and configuring the current includes configuring the current so as to increase an efficacy of the drug.

In an embodiment, configuring the current includes configuring the current to have an amplitude of between about 0.1 and about 15 milliamps. For some applications, configuring the current includes configuring the current to have an amplitude of between about 4 and about 15 milliamps.

In an embodiment, applying the current includes applying the current in respective bursts of pulses in each of a plurality of cardiac cycles of the subject. For some applications, configuring the current includes configuring each of the pulses to have a duration of between about 0.6 and about 2 milliseconds. For some applications, configuring the current includes configuring the pulses within each of the bursts to have a pulse repetition interval of between about 4 and about 20 milliseconds.

There is also provided, in accordance with an embodiment of the present invention, a method including:

selecting a subject who has not been diagnosed with any heart condition;

applying, for a period having a duration of at least about one month, a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current so as to not reduce a heart rate of the subject below a normal heart rate for a typical human.

In an embodiment, the method includes sensing a heart rate of the subject, and configuring the current includes configuring the current so as to reduce the heart rate towards the normal rate, responsive to a determination that the heart rate is greater than the normal rate.

In an embodiment, the method includes sensing a heart rate of the subject, and configuring the current includes configuring the current so as to minimize an effect of applying the current on the heart rate, responsive to a determination that the heart rate is within a desired range.

In an embodiment, the method includes sensing a physiological parameter of the subject, and configuring the current includes configuring the current so as to reduce the heart rate towards the normal rate, responsive to the physiological parameter.

There is further provided, in accordance with an embodiment of the present invention, a method for treating a subject suffering from a condition, including:

applying a current to a site of the subject selected from the list consisting of: a vagus nerve of the subject, and epicardial fat pad of the subject, a pulmonary vein of the subject, a carotid artery of the subject, a carotid sinus of the subject, a vena cava vein of the subject, and an internal jugular vein of the subject; and configuring the current so as to delay electrical remodeling of an atrium of the subject caused by the condition.

In an embodiment, configuring the current includes configuring the current so as to prevent electrical remodeling of the atrium caused by the condition.

In an embodiment, the condition includes heart failure (HF), and configuring the current includes configuring the current so as to prevent the electrical remodeling caused by the HF.

In an embodiment, the condition includes both atrial fibrillation (AF) and heart failure (HF), and configuring the current includes configuring the current so as to prevent the electrical remodeling caused by the AF and the HF.

In an embodiment, the method includes administering a drug for treating the condition.

In an embodiment, no drug is administered for treating the condition during a period beginning about 24 hours before initiation of application of the current and ending upon the initiation of the application of the current.

In an embodiment, the condition includes atrial fibrillation (AF), and configuring the current includes configuring the current so as to prevent the electrical remodeling caused by the AF. For some applications, applying the current includes detecting an occurrence of the AF, and applying the current responsively to the detecting. For some applications, applying the current includes applying the current not responsively to detecting an occurrence of the AF.

There is still further provided, in accordance with an embodiment of the present invention, a method for treating a subject susceptible to bradycardia, including:

administering to the subject a beta-blocker at a dosage lower than would normally be indicated for the subject;

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

sensing a heart rate of the subject; and upon detecting an occurrence of the bradycardia, terminating applying the current at least until a cessation of the bradycardia.

In an embodiment, applying the current includes applying the current in respective bursts of pulses in each of a plurality of cardiac cycles of the subject. For some applications, applying the current includes configuring each of the pulses to have a duration of between about 100 microseconds and about 1 millisecond. For some applications, applying the current includes configuring each of the bursts to have a duration of between about 1 and about 60 milliseconds. For some applications, applying the current includes configuring each of the bursts to contain between about 1 and about 5 pulses. For some applications, applying the current includes configuring the pulses within each of the bursts to have a pulse repetition interval of between about 1 and about 10 milliseconds. For some applications, applying the current includes configuring the pulses to have an amplitude of between about 0.1 and about 4 milliamps.

For some applications, applying the current includes applying the bursts once every second heartbeat. For some applications, applying the current includes applying the current to the site intermittently during alternating "on" and "off" periods, each of the "on" periods having a duration of at least about 500 milliseconds. For some applications, applying the current includes applying each of the bursts after a delay following an R-wave of the subject, the delay having a duration of between about 100 and about 700 milliseconds.

There is additionally provided, in accordance with an embodiment of the present invention, a method including:

applying a current to a site of a subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

applying a pacing signal to a heart of the subject; and configuring the pacing signal to substantially prevent any heart-rate-lowering effects of applying the current.

In an embodiment, applying the current includes applying the current to the site intermittently during alternating "on" and "off" periods, and configuring the pacing signal includes configuring the pacing signal to pace the heart at a rate that is approximately a rate of the heart during the "off" periods.

In an embodiment, applying the pacing signal includes sensing a post-stimulation-initiation heart rate of the subject after initiating application of the current, and applying the pacing signal when the post-stimulation-initiation heart rate is less than a threshold heart rate. For some applications, the method includes sensing a pre-stimulation-initiation heart rate of the subject prior to initiating application of the current, and setting the threshold heart rate equal to the pre-stimulation-initiation heart rate.

In an embodiment, applying the pacing signal includes continuing to apply the pacing signal during a period following termination of applying the current. For some applications, the period has a duration of less than about 30 seconds, and continuing to apply the pacing signal includes continuing to apply the pacing signal during the period having the duration of less than about 30 seconds.

There is yet additionally provided, in accordance with an embodiment of the present invention, a method including:

applying a current to a site of a subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current to reduce mechanical tension on at least one atrium of the subject, so as to reduce a risk of an occurrence of atrial fibrillation (AF).

In an embodiment, the method includes administering to the subject a drug for treating the AF.

There is also provided, in accordance with an embodiment of the present invention, a method for treating a subject suffering from an emergency condition, including:

administering atropine to the subject so as to treat the emergency condition;

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current so as to reduce an adverse effect sometimes caused by the atropine.

There is further provided, in accordance with an embodiment of the present invention, a method for treating a subject, including:

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current so as to treat a condition of the subject selected from the list consisting of: an autoimmune disease, an autoimmune inflammatory disease, multiple sclerosis, encephalitis, myelitis, immune-mediated neuropathy, myositis, dermatomyositis, polymyositis, inclusion body myositis, inflammatory demyelinating polyradiculoneuropathy, Guillain Barre syndrome, myasthenia gravis, inflammation of the nervous system, inflammatory bowel disease, Crohn's disease, ulcerative colitis, SLE (systemic lupus erythematosus), rheumatoid arthritis, vasculitis, polyarteritis nodosa, Sjogren syndrome, mixed connective tissue disease, glomerulonephritis, thyroid autoimmune disease, sepsis, meningitis, a bacterial infection, a viral infection, a fungal infection, sarcoidosis, hepatitis, and portal vein hypertension.

In an embodiment, the control unit is adapted to monitor a heart rate of the subject, and withhold the applying of the current in response to the heart rate being lower than a threshold heart rate.

There is still further provided, in accordance with an embodiment of the present invention, a method for treating a subject, including:

applying a current to a site of the subject selected from the list consisting of: a vagus nerve of the subject, and epicardial fat pad of the subject, a pulmonary vein of the subject, a carotid artery of the subject, a carotid sinus of the subject, a vena cava vein of the subject, and an internal jugular vein of the subject; and configuring the current so as to have an antiarrhythmic effect on an atrium of the subject.

For some applications, the site includes a right vagus nerve of the subject, and applying the current includes applying the current to the right vagus nerve.

In an embodiment, the method includes administering an antiarrhythmic drug to the subject in conjunction with applying the current.

For some applications, configuring the current includes configuring the current so as to induce rhythmic vagal activity in the subject.

There is additionally provided, in accordance with an embodiment of the present invention, a method for treating a subject suffering from heart failure (HF), including:

applying a current to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and configuring the current so as to decrease atrial contractile force of a heart of the subject, so as to treat the HF.

In an embodiment, applying the current includes applying the current to the site intermittently during alternating "on" and "off" periods. For some applications, applying the current intermittently includes setting each of the "on" periods to have a duration of between about 1 and about 15 seconds, and each of the "off" periods to have a duration of between about 5 and about 20 seconds.

In an embodiment, the site includes the vagus nerve, and applying the current includes applying the current to the vagus nerve. For some applications, applying the current includes applying a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, applying the current includes applying a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

In an embodiment, applying the current includes applying the current in respective bursts of pulses in each of a plurality of cardiac cycles of the subject. For some applications, applying the current includes applying a first pulse of each of the bursts after a delay from a sensed feature of an electrocardiogram (ECG) of the subject.

In an embodiment, the method includes sensing a physiological parameter of the subject, and configuring the current includes configuring the current at least in part responsively to the sensed physiological parameter. For some applications, sensing the physiological parameter includes sensing a heart rate of the subject.

In an embodiment, configuring the current includes configuring the current so as to minimize an effect of the applying of the current on a heart rate of the subject.

In an embodiment, applying the current includes applying the current in respective bursts of pulses in each of a plurality of cardiac cycles of the subject. For some applications, applying the current includes applying the current to a left vagus nerve of the subject. For some applications, applying the current includes configuring each of the pulses to have a duration of between about 200 microseconds and about 2.5 milliseconds. For some applications, applying the current includes configuring each of the pulses to have a duration of between about 2.5 and about 5 milliseconds. For some applications, applying the current includes configuring each of the bursts to have a duration of between about 0.2 and about 40 milliseconds. For some applications, applying the current includes configuring each of the bursts to contain between about 1 and about 10 pulses. For some applications, applying the current includes configuring the pulses within each of the bursts to have a pulse repetition interval of between about 2 and about 10 milliseconds. For some applications, applying the current includes configuring the pulses to have an amplitude of between about 0.5 and about 5 milliamps. For some applications, applying the current includes applying the bursts less than every heartbeat of the subject. For some applications, applying the current includes applying the bursts once per heartbeat of the subject. For some applications, applying the current includes applying the current to the site intermittently during alternating "on" and "off" periods, each of the "on" periods having a duration of at least about 1 second. For some applications, applying the current includes applying each of the bursts after a variable delay following a P-wave of the subject, the delay having a duration equal to between about two-thirds and about 90% of a duration of a cardiac cycle of the subject. For some applications, applying the current includes substantially continuously measuring the duration of the cardiac cycle.

In an embodiment, applying the current includes applying the current in respective bursts of pulses in each of a plurality of cardiac cycles of the subject. For some applications, applying the current includes configuring each of the pulses to have a duration of between about 100 microseconds and about 2.5 milliseconds. For some applications, applying the current includes configuring each of the bursts to have a duration of between about 1 and about 180 milliseconds. For some applications, applying the current includes configuring each of the bursts to contain between about 1 and about 10 pulses. For some applications, applying the current includes configuring the pulses within each of the bursts to have a pulse repetition interval of between about 1 and about 20 milliseconds. For some applications, applying the current includes configuring the pulses to have an amplitude of between about 0.1 and about 9 milliamps. For some applications, applying the current includes applying the bursts once every second heartbeat. For some applications, applying the current includes applying the bursts once every third heartbeat. For some applications, applying the current includes applying the current to the site intermittently during alternating "on" and "off" periods, each of the "on" periods having a duration of at least about 1 second. For some applications, applying the current includes applying each of the bursts after a delay following an R-wave of the subject, the delay having a duration of about 100 milliseconds.

In an embodiment, applying the current includes applying the current in respective bursts of between about 1 and about 10 pulses in each of a plurality of cardiac cycles of the subject, and applying a first pulse of each of the bursts after a delay of about 100 milliseconds after a sensed R-wave of an electrocardiogram (ECG) of the subject. For some applications, applying the current includes configuring each of the bursts to contain about three pulses. For some applications, applying the current includes varying a number of the pulses in each of the bursts responsive to a sensed parameter of a respiratory cycle of the subject. For some applications, applying the current includes varying a number of the pulses in each of the bursts responsive to a sensed heart rate of the subject. For some applications, the site includes the vagus nerve, and applying the current includes applying the current to the vagus nerve, and, responsive to a sensed heart rate of the subject, varying a number of nerve fibers of the vagus nerve that are recruited.

For some applications, the site includes the vagus nerve, and applying the current includes applying the current to the vagus nerve, and, responsive to a sensed parameter of a respiratory cycle of the subject, varying a number of nerve fibers of the vagus nerve that are recruited. For some applications, applying the current includes cycling between a first set of parameters and a second set of parameters. For some applications, cycling includes applying each set of parameters for less than about 15 seconds. For some applications, cycling includes applying each set of parameters for between about 1 and about 4 seconds. For some applications, the first set of parameters includes a first amplitude, the second set of parameters includes a second amplitude, greater than the first amplitude, and applying the current includes varying a number of nerve fibers of the vagus nerve that are recruited by cycling between the first set of parameters and the second set of parameters.

For some applications, cycling includes synchronizing application of the first set of parameters with inhalation by the subject, and synchronizing application of the second set of parameters with exhalation by the subject. For some applications, at least one of the first and second sets of parameters includes a pulse repetition interval of between about 4 and about 20 milliseconds, and applying the current includes cycling between the first and second sets of parameters. For some applications, at least one of the first and second sets of parameters includes a pulse width of between about 0.1 and about 2 milliseconds, and applying the current includes cycling between the first and second sets of parameters. For some applications, the first set of parameters includes application of the current at one pulse per each of the bursts, the second set of parameters includes application of the current at about three pulses per each of the bursts, and applying the current includes cycling between the first and second sets of parameters.

There is yet additionally provided, in accordance with an embodiment of the present invention, apparatus for treating a subject, including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:
drive the electrode device to apply an electrical current to the site, and
configure the current so as to enhance an efficacy of a drug administered to the subject for treating a condition from which the subject suffers selected from the list consisting of: atrial fibrillation (AF) and heart failure (HF).

There is also provided, in accordance with an embodiment of the present invention, a system for treating a subject, including:
a drug, adapted to be administered to the subject, and to treat a condition from which the subject suffers selected from the list consisting of: atrial fibrillation (AF) and heart failure (HF); and
apparatus including:
an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and
a control unit, adapted to:
drive the electrode device to apply an electrical current to the site, and
configure the current so as to enhance an efficacy of the drug.

There is further provided, in accordance with an embodiment of the present invention, apparatus for treating a subject suffering from a condition, including:
an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and
a control unit, adapted to:
drive the electrode device to apply an electrical current to the site, and
configure the current to increase vagal tone of the subject, and to minimize an effect of applying the current on a heart rate of the subject, so as to treat the condition.

There is still further provided, in accordance with an embodiment of the present invention, apparatus for treating a subject suffering from a condition, including:
an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and
a control unit, adapted to:
drive the electrode device to apply an electrical current to the site, and
configure the current so as to reduce an adverse effect sometimes caused by a drug administered to the subject for treating the condition.

There is additionally provided, in accordance with an embodiment of the present invention, a system for treating a subject suffering from a condition, including:
a drug, adapted to be administered to the subject, and to treat the condition; and
apparatus including:
an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and
a control unit, adapted to:
drive the electrode device to apply an electrical current to the site, and
configure the current so as to reduce an adverse effect sometimes caused by the drug.

There is yet additionally provided, in accordance with an embodiment of the present invention, apparatus for treating a subject, including:
an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and
a control unit, adapted to:
drive the electrode device to apply an electrical current to the site, and
configure the current so as to reduce a heart condition of the subject selected from the list consisting of: fibrosis of the heart, and inflammation of the heart.

For some applications, in an operating mode of the control unit, the control unit is adapted to drive the electrode device to apply the current during an application period lasting at least about three weeks, and to configure the current such that, during the application period, a longest duration of time in which no current is applied is less than four hours.

There is also provided, in accordance with an embodiment of the present invention, apparatus for treating a subject, including:
an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and
a control unit, adapted to:
drive the electrode device to apply an electrical current to the site, and
configure the current to inhibit propagation of naturally-generated efferent action potentials traveling through the site, while inhibiting no more than about 10% of naturally-generated afferent action potentials traveling through the site, so as to treat a condition of the subject.

There is further provided, in accordance with an embodiment of the present invention, apparatus for treating a subject who has not been diagnosed with any heart condition, including:
an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and
a control unit, adapted to:
drive the electrode device to apply an electrical current to the site for a period having a duration of at least about one month, and
configure the current so as to not reduce a heart rate of the subject below a normal heart rate for a typical human.

There is still further provided, in accordance with an embodiment of the present invention, apparatus for treating a subject suffering from a condition, including:
an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply an electrical current to the site, and configure the current so as to delay electrical remodeling of an atrium of the subject caused by the condition.

There is additionally provided, in accordance with an embodiment of the present invention, apparatus including:

a pacemaker, adapted to be coupled to a heart of a subject;

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply an electrical current to the site, drive the pacemaker to apply a pacing signal to the heart, and configure the pacing signal to substantially prevent any heart-rate-lowering effects of applying the current.

There is also provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply an electrical current to the site, and configure the current to reduce mechanical tension on at least one atrium of the subject, so as to reduce a risk of an occurrence of atrial fibrillation (AF).

There is further provided, in accordance with an embodiment of the present invention, apparatus for treating a subject, including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply an electrical current to the site, and configure the current so as to treat a condition of the subject selected from the list consisting of: an autoimmune disease, an autoimmune inflammatory disease, multiple sclerosis, encephalitis, myelitis, immune-mediated neuropathy, myositis, dermatomyositis, polymyositis, inclusion body myositis, inflammatory demyelinating polyradiculoneuropathy, Guillain Barre syndrome, myasthenia gravis, inflammation of the nervous system, inflammatory bowel disease, Crohn's disease, ulcerative colitis, SLE (systemic lupus erythematosus), rheumatoid arthritis, vasculitis, polyarteritis nodosa, Sjogren syndrome, mixed connective tissue disease, glomerulonephritis, thyroid autoimmune disease, sepsis, meningitis, a bacterial infection, a viral infection, a fungal infection, sarcoidosis, hepatitis, and portal vein hypertension.

There is still further provided, in accordance with an embodiment of the present invention, apparatus for treating a subject, including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply an electrical current to the site, and configure the current so as to have an antiarrhythmic effect on an atrium of the subject.

There is additionally provided, in accordance with an embodiment of the present invention, apparatus for treating a subject suffering from heart failure (HF), including:

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject; and a control unit, adapted to:

drive the electrode device to apply an electrical current to the site, and configure the current so as to decrease atrial contractile force of a heart of the subject, so as to treat the HF.

The present invention will be more fully understood from the following detailed description of embodiments thereof, taken together with the drawings, in which:

DETAILED DESCRIPTION OF EMBODIMENTS

Figure 1:
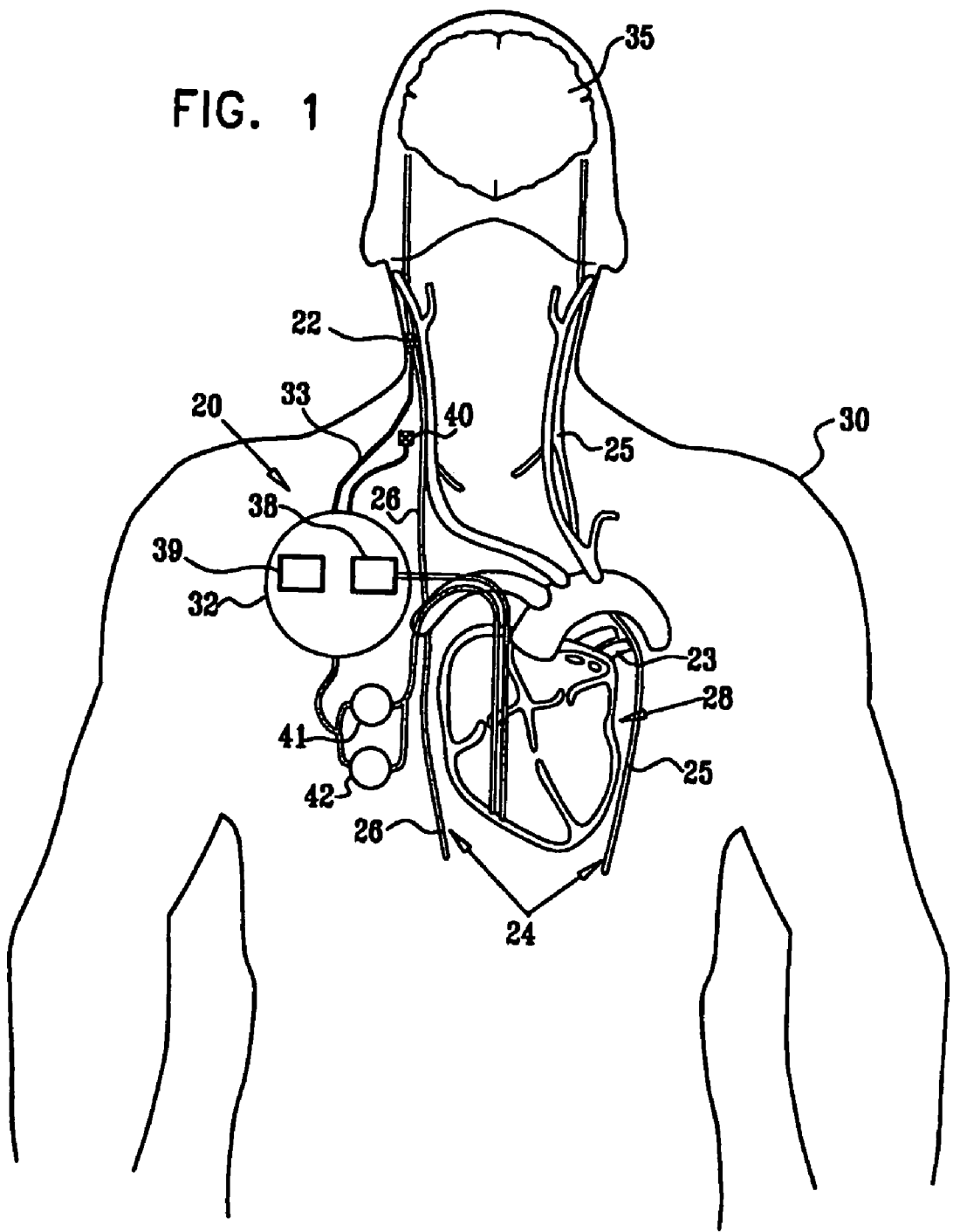
FIG. 1 is a schematic illustration of apparatus for treating a patient, in accordance with an embodiment of the present invention.

FIG. 1 is a schematic illustration of apparatus 20 for treating a patient 30, in accordance with an embodiment of the present invention. Apparatus 20 comprises at least one electrode device 22, which is applied to a vagus nerve 24 (either a left vagus nerve 25 or a right vagus nerve 26), which innervates a heart 28 of patient 30. Apparatus 20 further comprises an implanted or external control unit 32, which typically communicates with electrode device 22 over a set of leads 33. For some applications, apparatus 20 comprises two electrode devices 22, one of which is applied to left vagus nerve 25, and the other to right vagus nerve 26.

For some applications, as described hereinbelow, control unit 32 is adapted to drive electrode device 22 to apply signals to vagus nerve 26. The control unit configures these signals to induce the propagation of efferent nerve impulses towards heart 28. The control unit typically configures the signals based on the particular application, by setting one or more parameters of the signals, such as:

- frequency of pulses within a pulse burst, e.g., for n pulses during a burst lasting t milliseconds, the burst has a frequency of 1000 n/t Hz;
- amplitude;
- pulse width;
- number of pulse delivered per heartbeat (pulses per trigger, or PPT);
- duty cycle;
- pulse polarity; and
- timing within the cardiac cycle.

Control unit 32 is typically adapted to receive and analyze one or more sensed physiological parameters or other parameters of patient 30, such as ventricular and/or atrial rate, electrocardiogram (ECG), blood pressure, indicators of decreased cardiac contractility, cardiac output, norepinephrine concentration, baroreflex sensitivity, or motion of the patient. In order to receive these sensed parameters, control unit 32 may comprise, for example, an ECG monitor 38, connected to a site on the patient's body such as heart 28, for example using one or more subcutaneous sensors or ventricular and/or atrial intracardiac sensors. The control unit may also comprise an accelerometer 39 for detecting motion of the patient. Alternatively, ECG monitor 38 and/or accelerometer 39 comprise separate implanted devices placed external to control unit 32, and, optionally, external to the patient's body. Alternatively or additionally, control unit 32 receives signals from one or more physiological sensors 40, such as blood pressure sensors. For some applications, control unit 32 comprises or is coupled to an implantable cardioverter defibrillator (ICD) 41 and/or a pacemaker 42 (e.g., a bi-ventricular or standard pacemaker).

For some applications, control unit 32 is adapted to distinguish between AF and NSR, generally by analyzing an ECG signal generated by ECG monitor 38. In order to detect rapid atrial activity indicative of AF, the analysis may include one or more of the following:

- P-wave analysis;
- analysis of ventricular response rate and/or ventricular response variability;
- sensed pressure, such as atrial pressure, sensed venous pressure, and/or sensed arterial pressure;
- the relationship(s) between one or more of the sensed pressures and sensed ventricular contractions (in the case of arterial pressure, such relationship is an indication of pulse deficit); and/or
- analysis of the duration of the isoelectrical segment of the ECG, optionally using the technique described in the above-cited article by Wijffels et al., entitled, "Atrial fibrillation begets atrial fibrillation." A duration greater than a first threshold value is typically indicative of NSR, while a duration less than a second threshold value, the second threshold value less than or equal to the first threshold value, is typically indicative of AF.

Control unit 32 itself may perform this analysis, or it may transmit data for analysis by an external processor (not shown).

Typically, apparatus 20 is programmable by a physician, such as by using an external console wirelessly in communication with control unit 32. The apparatus typically provides notification of various occurrences, such as the initiation of AF, the initiation of treatment, or a mechanical failure. The apparatus may provide such notifications by various means, including generating a tone, vibrating, and/or wirelessly communicating with a local or remote receiver, such as one located at a medical facility.

For some applications of vagal stimulation, control unit 32 applies the signals to vagus nerve 24 as a burst of pulses during each cardiac cycle, with one or more of the following parameters (collectively, these parameters are referred to hereinbelow as "typical stimulation parameters"):

- Timing of the stimulation: for example, each pulse may be initiated at about 100 milliseconds after an R-wave.
- Pulse duration: each pulse typically has a duration of between about 100 microseconds and about 2.5 milliseconds, e.g., about 1 millisecond.
- Pulse amplitude: the pulses are typically applied with an amplitude of between about 0.1 and about 9 milliamps, e.g., about 2.5 milliamps.
- Pulse repetition interval: the pulses within the burst of pulses typically have a pulse repetition interval (the time from the initiation of a pulse to the initiation of the following pulse) of between about 1 and about 20 milliseconds, e.g., about 6 milliseconds.
- Pulses per trigger (PPT): the burst of pulses typically contains between about 1 and about 10 pulses, e.g., 3 pulses.
- Pulse period, i.e., burst duration (equal to the product of pulse repetition interval and PPT): the burst of pulses typically has a total duration of between about 1 and about 180 milliseconds.
- Duty cycle: stimulation is typically applied once per heartbeat, once every second heartbeat, or once every third heartbeat.
- On/off status: for some applications, stimulation is always "on", i.e., constantly applied (in which case, parameters closer to the lower ends of the ranges above are typically used). For other applications, on/off cycles vary between a few seconds to several minutes, e.g., "on" for 15 seconds, "off" for 60 seconds.

In an embodiment of the present invention, a method for enhancing or sustaining the efficacy of drug treatment for atrial fibrillation (AF) comprises administering a drug to patient 30 and applying signals to a vagus nerve that innervates heart 28 of the patient. The drug administered typically includes either:

- a sinus rhythm maintenance drug (i.e., an antiarrhythmic drug), such as a beta-blocker, digoxin, amiodarone, disopyramide, dofetilide, a class IC drug (e.g., flecainide, propafenone), procainamide, quinidine, or sotalol; or
- a ventricular rate control drug, such as a beta-blocker (e.g., esmolol), calcium channel antagonists (e.g., verapamil, diltiazem), or digoxin.

According to this method, the efficacy of the drug is typically enhanced or sustained by (a) configuring the signals so as to prevent electrical remodeling of the atria, which remodeling generally reduces drug effectiveness over time, (b) configuring the signals so as to achieve a therapeutic benefit similar to that of the drug, which typically results in a synergistic effect between the therapeutic benefit of the drug and the vagal stimulation, and/or (c) configuring the signals so as to reduce the mechanical tension on the atria.

Atrial electrical remodeling, i.e., electrophysiological changes to the atria, commonly occurs in patients suffering from AF. Such electrical remodeling is believed to be caused by the underlying heart condition that instigated the AF, and/or by the effect of the AF itself on the atria (see the above-cited article entitled, "Atrial fibrillation begets atrial fibrillation," by Wijffels et al.). As electrical remodeling becomes more severe, relapses into AF become more frequent and difficult to prevent. As a result, drug therapy for preventing such relapses becomes less effective. Vagal stimulation, using techniques described herein, typically delays or prevents (i.e., delays indefinitely) electrical remodeling, thereby prolonging the effectiveness of antiarrhythmic drugs. For some applications, control unit 32 configures the signals applied to the vagus nerve using parameters described hereinbelow for applying vagal stimulation with minimum heart rate reduction.

In an embodiment of the present invention, vagal stimulation is applied in combination with administration of a drug, as described in the following examples:

In Combination with Beta-blockers

A beta-blocker is administered substantially at its usual dosage (i.e., at a dosage determined independently of applying the vagal stimulation), and vagal stimulation is applied using parameters described hereinbelow for applying vagal stimulation with minimum heart rate reduction.

For Bradycardia

For treating a patient susceptible to bradycardia, a beta-blocker is administered at a dosage lower than would normally be indicated, and vagal stimulation is applied using parameters described hereinbelow for applying vagal stimulation with minimum heart rate reduction, or using parameters at the lower range of the typical stimulation parameters described hereinabove. Upon detection of bradycardia, the vagal stimulation is terminated.

In Combination with a Sinus Rhythm Maintenance Drug

A patient who suffers from AF is treated by conventional cardioversion and a sinus rhythm maintenance drug, such as quinidine. To enhance the desired effect of the drug, the drug is administered in conjunction with the application of rhythmic vagal stimulation. The resulting rhythmic, synchronized vagal activity generally mimics normal vagal traffic, which is sometimes reduced in these patients (who may, for example, suffer from heart failure or hypertension). Stable NSR typically results from the combined treatment modalities, thereby generally reducing the occurrence of AF.

Parameters of such rhythmic vagal stimulation typically include all or some of the following: (a) application of the stimulation as bursts synchronized with the patient's cardiac cycle, with each burst typically beginning at about 100 milliseconds after an R-wave, (b) about three pulses per burst (i.e., per cardiac cycle), (c) varying the number of pulses per burst responsive to sensed parameters of the patient's respiratory cycle or heart rate, and (d) varying the number of nerve fibers recruited responsive to sensed parameters of the patient's respiratory cycle or heart rate.

For example, vagal stimulation may be applied by cycling between a first set and a second set of parameters, applying each set for less than about 15 seconds, e.g., for between about 1 and about 4 seconds. The first set of parameters may include: (a) a low amplitude, e.g., 2 milliamps, so as to recruit a relatively small number of nerve fibers, (b) optional synchronization with inhalation, and (c) one pulse per trigger (PPT), for example applied at about 300 milliseconds after an R-wave. The second set of parameters may include: (a) a greater amplitude, e.g., 3 milliamps, so as to recruit a greater number of fibers, (b) optional synchronization with exhalation, and (c) three PPT, applied at about 300 milliseconds after an R-wave. Both sets of parameters optionally include a pulse width of about 1 millisecond and/or a pulse repetition interval of between about 4 and about 20 milliseconds.

In Combination with a Positive Inotropic Agent

A positive inotropic agent is administered for longer than one day, and vagal stimulation is applied using techniques described herein, using the typical stimulation parameters described hereinabove. Without the use of the vagal stimulation techniques described herein, drugs of this class (with the exception of digitalis) are generally administered only in an acute setting. In combination with vagal stimulation as described herein, however, the administration of the positive inotropic agent is hypothesized by the inventors to have the same or enhanced effect, without its chronotropic and proarrhythmic (ventricular) effects. In addition, it is hypothesized that in combination with vagal stimulation as described herein, the positive effects of the positive inotropic agent do not decline, or decline less, over time, when administered on a long-term basis.

For treating a stable patient, a positive inotropic agent is administered, and vagal stimulation is applied using parameters described hereinbelow for applying vagal stimulation with minimum heart rate reduction, or using the typical stimulation parameters described hereinabove. Without the use of the vagal stimulation techniques described herein, drugs of this class are generally not routinely used because of evidence indicating increased mortality mainly attributable to ventricular arrhythmia. Use of the vagal stimulation techniques described herein typically reduces the incidence of ventricular arrhythmia, thereby enabling the use of drugs of this class for longer-term treatment of stable patients.

For Emergency Settings

In order to increase heart rate in an emergency setting (e.g., bradycardia and/or shock), atropine is administered, and vagal stimulation is applied, using the typical stimulation parameters described hereinabove, in order to increase heart rate and cardiac output.

In Combination with a Class IC Drug

A class IC drug is administered at a dosage greater than would normally be indicated or considered safe, and vagal stimulation is applied using parameters described hereinbelow for applying vagal stimulation with minimum heart rate reduction, or using the typical stimulation parameters described hereinabove, to counteract at least some of the side effects of the class IC drug.

In an embodiment of the present invention, vagal stimulation configured for inhibiting, delaying or preventing (i.e., delaying indefinitely) electrical remodeling in AF patients is applied in the absence of specific antiarrhythmic drug therapy. Such prevention of electrical remodeling alone is believed by the inventors to be therapeutically beneficial. For example, Takei et al., in their above-cited article, hypothesize, based on their experiments in anesthetized dogs, that vagal stimulation prior to atrial rapid pacing may protect the atrium from electrical remodeling.

In an embodiment of the present invention, a method for enhancing or sustaining the efficacy of a drug treatment for AF comprises administering a drug to the patient, applying signals to the vagus nerve, and configuring the signals to reduce the mechanical tension on the atria. Such reduced mechanical tension generally reduces the risk of AF. For some applications, such vagal stimulation is applied without administering the drug.

For some applications, such vagal stimulation for the prevention of atrial remodeling (whether or not in conjunction with drug therapy) is applied generally constantly, using parameters described hereinbelow for applying vagal stimulation with minimum heart rate reduction, or using the typical stimulation parameters described hereinabove. For other applications, such stimulation is only applied upon the detection of the occurrence of AF, such as by using one or more of the AF detection techniques described hereinabove.

In an embodiment of the present invention, control unit 32 configures the signals applied to the vagus nerve to have an antiarrhythmic effect on the atrium. Typical signal parameters in such a configuration include those described hereinbelow for applying vagal stimulation with minimum heart rate reduction, or the typical stimulation parameters described hereinabove. The stimulation is typically applied to right vagus nerve 26, but may also be applied to left vagus nerve 25 or both vagus nerves together. For some applications, such antiarrhythmic vagal stimulation is applied in conjunction with the rhythmic vagal stimulation technique described hereinabove. For applications in which such antiarrhythmic vagal stimulation is applied in combination with antiarrhythmic drug therapy, the combined treatment generally results in a synergistic effect.

In another embodiment of the present invention, the effectiveness of ventricular rate control drugs is typically enhanced by applying vagal stimulation in order to control the ventricular response rate. Such combined vagal stimulation and drug therapy generally results in a synergistic effect. Vagal stimulation techniques for controlling ventricular response rate may be used that are described in U.S. patent application Ser. No. 10/205,475, filed Jul. 24, 2002, entitled, "Selective nerve fiber stimulation for treating heart conditions," which is assigned to the assignee of the present patent application and is incorporated herein by reference, or by using other techniques known in the art.

In an embodiment of the present invention, the safety of a drug administered to patient 30 is improved by applying signals to vagus nerve 24, and configuring the signals so as to prevent adverse effects sometimes caused by the drug, such as repolarization abnormalities (e.g., prolongation of the QT interval), bradycardia, and/or ventricular tachyarrhythmia (e.g., ventricular fibrillation). In some cases, the drug can safely be administered to patients who otherwise could not tolerate the drug because of such adverse effects. (See, for example, the above-cited article by Kwan et al., which discusses the limitations side effects sometimes impose on drug success). In addition, in some cases adverse effects of the drug are prevented or diminished by allowing the use of lower dosages of the drug (i.e., dosages lower than dosages determined independently of applying the vagal stimulation), by enhancing or sustaining the efficacy of the drug, as described hereinabove. For example, toxicity associated with digoxin may be prevented or reduced by enabling a lower dosage using these stimulation techniques.

Prolongation of the QT interval is an adverse effect sometimes caused by antiarrhythmic drugs. Vagal stimulation, using techniques described herein, typically shortens the QT interval, thereby offsetting the QT prolongation caused by such drugs. As a result, such drugs are generally safer, and, in some cases, more effective. In addition, such increased safety allows for the use of higher dosages of such drugs, if therapeutically indicated. For some applications, in order to obtain the QT interval reduction, and/or to prevent other side effects, such as abdominal pain, diarrhea, or ventricular arrhythmia not related to the QT interval, control unit 32 configures the signals applied to the vagus nerve using parameters described hereinbelow for applying vagal stimulation with minimum heart rate reduction.

Bradycardia is an adverse effect sometimes caused by antiarrhythmic drugs and heart rate control drugs. The use of a lower dosage of such drugs enabled by vagal stimulation techniques described herein generally reduces the likelihood of bradycardia, while obtaining a beneficial effect similar to that achieved at higher drugs dosages without such vagal stimulation. This vagal stimulation is typically applied using techniques described herein for minimizing reductions in heart rate as a result of the stimulation. In addition, in an embodiment, apparatus 20 monitors heart rate, such as by using ECG monitor 38, and, upon detection of bradycardia, activates pacemaker 42 to pace the heart. Alternatively or additionally, upon detection of bradycardia, apparatus 20 terminates or reduces the intensity of vagal stimulation.

Ventricular tachyarrhythmia is an adverse effect sometimes caused by antiarrhythmic drugs or positive inotropic drugs. Vagal stimulation, using techniques described herein, typically reduces or prevents tachyarrhythmia, premature ventricular contractions, ventricular tachycardia, accelerated idioventricular arrhythmia, and/or ventricular fibrillation, by reducing the propensity of cardiac tissue to spontaneously fire.

In an embodiment of the present invention, a method for enhancing or sustaining the efficacy of drug treatment for heart failure comprises administering a drug to patient 30 and applying signals to vagus nerve 24 that innervates heart 28 of the patient. The signals are configured so as to treat the heart failure, which typically results in a synergistic effect between the therapeutic benefit of the drug and the vagal stimulation. For example, the drug may include positive inotropic drugs such as digoxin, dopamine, dobutamine, adrenaline, amrinone, or milrinone.

Alternatively or additionally, the signals are configured so as to prevent adverse effects sometimes caused by the heart failure drug, such as ventricular arrhythmia and/or ventricular tachycardia. For some applications, ventricular tachycardia is prevented using techniques described hereinabove for controlling ventricular response rate using vagal stimulation. For some applications, arrhythmia is prevented by elevation of vagal tone and application of rhythmic synchronized vagal stimulation, for example using the parameters for rhythmic vagal stimulation described hereinabove.

In addition, in some cases adverse effects of the heart failure drug are prevented or diminished by allowing the use of lower dosages of the drug because of the synergistic effect of the vagal stimulation with the drug treatment.

In an embodiment of the present invention, a method for enhancing or sustaining the efficacy of antithrombotic therapy comprises administering an antithrombotic drug to patient 30 and applying signals to vagus nerve 24 that innervates heart 28 of the patient. The signals are configured so as to increase atrial motion, which typically results in a synergistic effect between the therapeutic benefit of the drug and the vagal stimulation. Such vagal stimulation thus may (a) increase the efficacy of the antithrombotic drug, and/or (b) allow the use of a lower dosage of the drug, without reducing the efficacy of the drug. As used in the present patent application including the claims, antithrombotic drugs are to be understood as drugs that are intended to reduce the risk of thromboembolic events, including, but not limited to, anticoagulation drugs that inhibit the coagulation cascade (e.g., warfarin, heparin, low molecular weight heparin (LMWH)), and drugs that inhibit platelet aggregation (e.g., aspirin and clopidogrel). Increased efficacy caused by vagal stimulation may increase the effectiveness of a platelet aggregation inhibition drug, thereby allowing the use of such a drug instead of anticoagulation drugs, which typically have greater side effects and risks, and require more precise dosaging, than platelet aggregation inhibition drugs. In addition, use of a lower dosage may reduce complications associated with typical dosages of antithrombotic drugs. For antithrombotic drug regimens in which dosages are selected to achieve a target international normalized ratio (INR) of 2.5, the synergistic effect of the vagal stimulation with the drug treatment may allow the same beneficial effect to be achieved at a lower INR, e.g., 1.5, thereby reducing drug complications. For some applications, antithrombotic therapy is enhanced or sustained by elevation of vagal tone and application of rhythmic synchronized vagal stimulation, for example using the parameters for rhythmic vagal stimulation described hereinabove.

In an embodiment of the present invention, vagal stimulation is applied and configured to prevent atrial electrical remodeling caused by heart failure (see the above-cited article by Li D et al.). For some applications, such stimulation is applied to increase the efficacy and/or safety of a heart failure drug; for other applications, such stimulation is applied in the absence of specific drug therapy. Such prevention of electrical remodeling alone is believed by the inventors to be therapeutically beneficial. In an embodiment, vagal stimulation is applied and configured to treat a patient suffering from both AF and heart failure, such as by preventing atrial electrical remodeling, and/or by increasing the efficacy and/or safety of one or more drugs for AF and/or heart failure.

In an embodiment of the present invention, a method for enhancing the efficacy of drug treatment for heart failure comprises administering a "preload reduction" drug, such as an ACE inhibitor, nitrate, or sodium nitroprusside, to patient 30, and applying signals to vagus nerve 24 that innervates heart 28 of the patient. Such preload reduction drugs are intended to reduce the pressure in the venous system. During heart failure, atrial contraction sometimes pushes blood back into the venous and pulmonary systems. To minimize this unwanted effect, the signals applied to the vagus nerve are configured so as to decrease atrial contractile force, using the typical stimulation parameters described hereinabove, for example with a short "on" time (e.g., between about 1 and about 15 seconds) and a longer "off" time (e.g., between about 5 and about 20 seconds). For some applications, the "on" and "off" times are equal, and for other applications, the "off" time is longer than the "on" time. In an embodiment, this vagal stimulation treatment is applied without the preload reduction drug treatment.

In an embodiment of the present invention, a method for increasing vagal tone comprises applying signals to vagus nerve 24, and configuring the signals to stimulate the vagus nerve, thereby delivering parasympathetic nerve stimulation to heart 28, while at the same time minimizing the heart-rate-lowering effects of the stimulation. Such treatment generally results in the beneficial effects of vagal stimulation that are not necessarily dependent on the heart-rate reduction effects of such stimulation. (See, for example, the above-cited article by Vanoli E et al.) Therefore, such vagal stimulation is generally useful for treating conditions such as AF, heart failure, atherosclerosis, restenosis, myocarditis, cardiomyopathy, post-myocardial infarct remodeling, and hypertension. In addition, such treatment is believed by the inventors to reduce the risk of sudden cardiac death in some patients (such as those with hypertrophic cardiomyopathy or congenital long QT syndrome). Furthermore, such treatment is believed by the inventors to be beneficial for the treatment of some non-cardiovascular conditions, such as an autoimmune disease, an autoimmune inflammatory disease, multiple sclerosis, encephalitis, myelitis, immune-mediated neuropathy, myositis, dermatomyositis, polymyositis, inclusion body myositis, inflammatory demyelinating polyradiculoneuropathy, Guillain Barre syndrome, myasthenia gravis, inflammation of the nervous system, SLE (systemic lupus erythematosus), rheumatoid arthritis, vasculitis, polyarteritis nodosa, Sjogren syndrome, mixed connective tissue disease, glomerulonephritis, thyroid autoimmune disease, sepsis, meningitis, a bacterial infection, a viral infection, a fungal infection, sarcoidosis, hepatitis, and portal vein hypertension, obesity, constipation, irritable bowl syndrome, rheumatoid arthritis, glomerulonephritis, hepatitis, pancreatitis, thyroiditis, type I diabetes, and type II diabetes. For some applications, conditions mentioned in this paragraph are treated by applying vagal stimulation, and not necessarily minimizing the heart-rate-lowering effects of the stimulation.

Such vagal stimulation is also beneficial for treating some conditions or under some circumstances in which heart rate reduction is not indicated or is contraindicated. For example, such vagal stimulation is typically appropriate:

- for treating heart failure patients that suffer from bradycardia when taking beta-blockers;
- at nighttime, when heart rate is naturally lower;
- during exercise, such as when the heart rate is already within a desired range and further decreases may reduce exercise tolerance;
- for patients receiving heart-rate lowering drugs, who have achieved a heart rate within a desired range prior to beginning vagal stimulation, and therefore would not benefit from further heart rate reduction;
- for patients suffering from low cardiac output, for whom heart rate reduction may further reduce cardiac output;
- during acute myocardial infarction with cardiogenic shock;
- for patients who experience discomfort or a reduction in exercise capacity when the heart rate is reduced; and
- for patients having a tendency towards bradycardia when receiving vagal stimulation.

In an embodiment of the present invention, in order to increase vagal tone while at the same time minimizing or preventing the heart-rate-lowering effects of the stimulation, control unit 32 applies the signals to the vagus nerve as a burst of pulses during each cardiac cycle, with one or more of the following parameters:

Timing of the stimulation: delivery of the burst of pulses begins after a variable delay following each P-wave, the length of the delay equal to between about two-thirds and about 90% of the length of the patient's cardiac cycle. Such a delay is typically calculated on a real-time basis by continuously measuring the length of the patient's cardiac cycle.

Pulse duration: each pulse typically has a duration of between about 200 microseconds and about 2.5 milliseconds for some applications, or, for other applications, between about 2.5 milliseconds and about 5 milliseconds.

Pulse amplitude: the pulses are typically applied with an amplitude of between about 0.5 and about 5 milliamps, e.g., about 1 milliamp.

Pulse repetition interval: the pulses within the burst of pulses typically have a pulse repetition interval (the time from the initiation of a pulse to the initiation of the following pulse) of between about 2 and about 10 milliseconds, e.g., about 2.5 milliseconds.

Pulse period: the burst of pulses typically has a total duration of between about 0.2 and about 40 milliseconds, e.g., about 1 millisecond.

Pulses per trigger (PPT): the burst of pulses typically contains between about 1 and about 10 pulses, e.g., about 2 pulses.

Vagus nerve: the left vagus nerve is typically stimulated in order to minimize the heart-rate-lowering effects of vagal stimulation.

Duty cycle: stimulation is typically applied only once every several heartbeats, or once per heartbeat, when a stronger effect is desired.

On/off status: for some applications, stimulation is always "on", i.e., constantly applied (in which case, parameters closer to the lower ends of the ranges above are typically used). For other applications, on/off cycles vary between a few seconds to several dozens of seconds, e.g., "on" for about 36 seconds, "off" for about 120 seconds, "on" for about 3 seconds, "off" for about 9 seconds.

For example, vagal stimulation may be applied to a patient having a heart rate of 60 BPM, with the intention of minimally reducing the patient's heart rate. The burst of pulses may be delivered beginning about 750 milliseconds after each R-wave of the patient. The stimulation may be applied with one pulse per trigger (PPT), and having an amplitude of 1 milliamp. The stimulation may be cycled between "on" and "off" periods, with each "on" period having a duration of about two seconds, i.e., two heart beats, and each "off" period having a duration of about 4 seconds.

Alternatively or additionally, the control unit drives pacemaker 42 to pace the heart, so as to prevent any heart-rate lowering effects of such vagal stimulation. Typically, the control unit paces the heart at a rate that is similar to the rate when the device is in "off" mode. Control unit 32 then applies signals to vagus nerve 24, typically using the typical stimulation parameters described hereinabove. This vagal stimulation generally does not lower the heart rate, because of the pacemaker pacing. For some applications, control unit 32 applies signals to vagus nerve 24, and senses the heart rate after applying the signals. The control unit drives pacemaker 42 to pace the heart if the sensed heart rate falls below a threshold heart rate. The threshold heart rate is typically equal to a heart rate of the patient prior to commencing the vagal stimulation, for example, as sensed by control unit 32. The control unit thus typically maintains the heart rate at a rate above a bradycardia threshold rate, unlike conventional pacemakers which are typically configured to pace the heart only when the rate falls below a bradycardia threshold rate. Upon termination of vagal stimulation, control unit 32 typically drives pacemaker 42 to continue pacing the heart for a period typically having a duration between about 0 and about 30 seconds, such as about 5 seconds.

In an embodiment of the present invention, control unit 32 drives pacemaker 42 to pace the heart, and configures the signals applied to the vagus nerve using the typical stimulation parameters described hereinabove. For some applications, the higher ends of the ranges of values for one or more of these parameters are applied. The use of the pacemaker generally prevents any heart-rate-lowering effects of such vagal stimulation.

In an embodiment of the present invention, control unit 32 applies minimal-heart-rate-lowering stimulation using a feedback loop. The control unit calculates an average heart rate (ventricular and/or atrial rate) of the subject. The control unit then applies signals to vagus nerve 24, using the minimal heart rate reduction parameters described hereinabove. During such stimulation, the control unit substantially continuously monitors the resulting heart rate. If the heart rate declines by more than a certain percentage (e.g., by more than about 5%, such as from 100 BPM to 90 BPM), the control unit adjusts the stimulation parameters in order to further minimize the heart-rate-lowering effect of the stimulation. For example, the control unit may adjust the stimulation parameters by reducing the amplitude of the stimulation, changing the timing of the stimulation, reducing the frequency of the stimulation, reducing the duration of each pulse, and/or reducing the duration of the stimulation period.

In an embodiment of the present invention, a method for preventing or reducing fibrosis and/or inflammation of the heart comprises configuring control unit 32 to apply signals to vagus nerve 24 that innervates heart 28 of the patient. Substantially continuous application of such stimulation generally modulates immune system responses, thereby reducing atrial, ventricular, and/or coronary inflammation and/or fibrosis. Such stimulation is typically applied using the typical stimulation parameters described hereinabove, or the parameters described hereinabove for minimal heart rate reduction. For some applications, such stimulation is applied for more than about three weeks. Conditions that are believed to be at least partially immune-modulated, and therefore to generally benefit from such vagal stimulation, include, but are not limited to, atrial and ventricular remodeling (e.g., induced by AF, heart failure, myocarditis, and/or myocardial infarct), restenosis, and atherosclerosis.

In an embodiment of the present invention, control unit 32 is configuring to apply signals to vagus nerve 24 of patient 30, and the signals are configured to inhibit propagation of naturally-generated efferent action potentials in the vagus nerve. Typically, the signals are additionally configured to inhibit no more than about 10% of naturally-generated afferent action potentials traveling through the vagus nerve. It is hypothesized by the inventors that such inhibition is useful for treating AF, typically by enhancing drug efficacy, and for preventing bradycardia.

In an embodiment of the present invention, electrical signals are applied by electrode device 22, typically on a long-term basis, to vagus nerve 24 of a subject not necessarily suffering from a heart condition, in order to increase the life expectancy, quality of life, and/or healthiness of the subject. Such signals are typically configured to not reduce the heart rate below normal range for a typical human. Typical parameters of such stimulation include those described hereinabove for minimal heart-rate-reducing stimulation, for periods during which the heart rate is at a desired level, and those described hereinabove for lowering heart rate, when it is desired to lower the heart rate from above normal to normal. For some applications, a determination regarding whether to attempt to lower the heart rate is made responsive to physiological parameters sensed using a sensor, such as an activity sensor, a respiration sensor, or accelerometer 39. Such chronic vagal stimulation is hypothesized by the inventors to be effective for increasing life expectancy, quality of life, and/or healthiness by (a) causing a reduction in cardiovascular disease and/or events, (b) having an anti-inflammatory effect, (c) reducing heart rate from faster than desirable to desirable normal rates, (d) reducing metabolic rate, and/or (e) generally having a calming and relaxing effect.

For many of the applications of vagal stimulation described herein, electrode device 22 typically comprises one or more electrodes, such as monopolar, bipolar or tripolar electrodes. Electrode device 22 is typically placed: (a) around vagus nerve 24, (b) around vagus nerve 24 and the carotid artery (configuration not shown), or (c) inside the carotid artery in a position suitable for vagal stimulation (not shown). Depending on the particular application, one or more electrode devices 22 may be positioned to stimulate the left or right vagus nerve, either above or below the cardiac branch bifurcation. For some applications, the electrodes comprise cuff electrodes, ring electrodes, and/or point electrodes. Typically, the electrodes stimulate the nerve without coming in direct contact therewith, by applying an electrical field to the nerve. Alternatively, the electrodes stimulate the nerve by coming in direct contact therewith. Control unit 32 typically configures the signals to induce the propagation of efferent nerve impulses towards heart 28.

In some embodiments of the present invention, when configuring vagal stimulation to induce the propagation of efferent nerve impulses towards heart 28, control unit 32 drives electrode device 22 to (a) apply signals to induce the propagation of efferent nerve impulses towards heart 28, and (b) suppress artificially-induced afferent nerve impulses towards a brain 35 of the patient (FIG. 1), in order to minimize unintended side effects of the signal application.

Figure 2A:
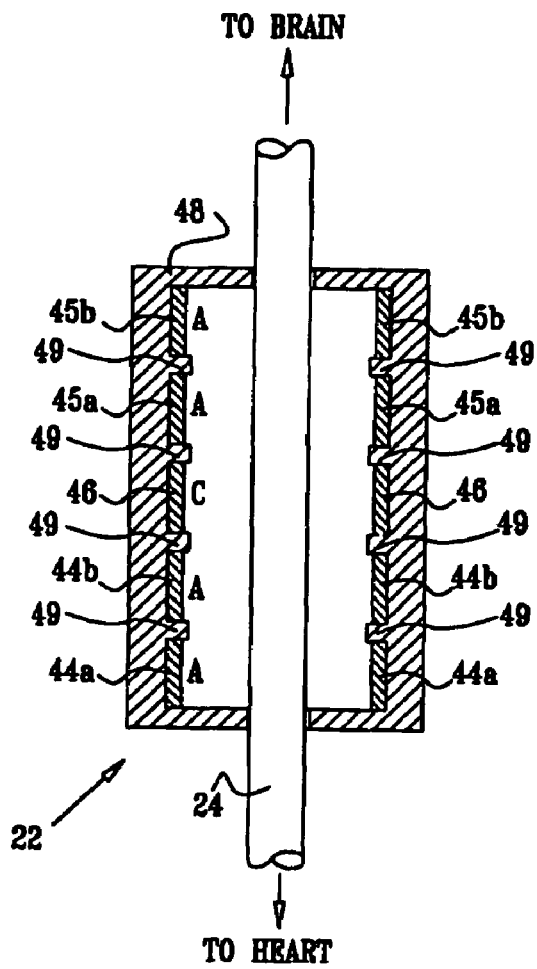
FIG. 2A is a simplified cross-sectional illustration of a multipolar electrode device applied to a vagus nerve, in accordance with an embodiment of the present invention.

FIG. 2A is a simplified cross-sectional illustration of a generally-cylindrical electrode device 22 applied to vagus nerve 24, in accordance with an embodiment of the present invention. Electrode device 22 comprises a central cathode 46 for applying a negative current ("cathodic current") in order to stimulate vagus nerve 24, as described below. Electrode device 22 additionally comprises a set of one or more anodes 44 (44a, 44b, herein: "efferent anode set 44"), placed between cathode 46 and the edge of electrode device 22 closer to heart 28 (the "efferent edge"). Efferent anode set 44 applies a positive current ("efferent anodal current") to vagus nerve 24, for blocking action potential conduction in vagus nerve 24 induced by the cathodic current, as described below. Typically, electrode device 22 comprises an additional set of one or more anodes 45 (45a, 45b, herein: "afferent anode set 45"), placed between cathode 46 and the edge of electrode device 22 closer to brain 35. Afferent anode set 45 applies a positive current ("afferent anodal current") to vagus nerve 24, in order to block propagation of action potentials in the direction of the brain during application of the cathodic current.

For some applications, the one or more anodes of efferent anode set 44 are directly electrically coupled to the one or more anodes of afferent anode set 45, such as by a common wire or shorted wires providing current to both anode sets, substantially without any intermediary elements. Typically, the sizes of the anodes and/or distances of the various anodes from the nerve are regulated so as to produce desired ratios of currents delivered through the various anodes. In these applications, central cathode 46 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Cathode 46 and anode sets 44 and 45 (collectively, "electrodes") are typically mounted in a housing such as an electrically-insulating cuff 48 and separated from one another by insulating elements such as protrusions 49 of the cuff. Typically, the width of the electrodes is between about 0.5 and about 2 millimeters, or is equal to approximately one-half the radius of the vagus nerve. The electrodes are typically recessed so as not to come in direct contact with vagus nerve 24. For some applications, such recessing enables the electrodes to achieve generally uniform field distributions of the generated currents and/or generally uniform values of the activation function defined by the electric potential field in the vicinity of vagus nerve 24. Alternatively or additionally, protrusions 49 allow vagus nerve 24 to swell into the canals defined by the protrusions, while still holding the vagus nerve centered within cuff 48 and maintaining a rigid electrode geometry. For some applications, cuff 48 comprises additional recesses separated by protrusions, which recesses do not contain active electrodes. Such additional recesses accommodate swelling of vagus nerve 24 without increasing the contact area between the vagus nerve and the electrodes. For some applications, the distance between the electrodes and the axis of the vagus nerve is between about 1 and about 4 millimeters, and is greater than the closest distance from the ends of the protrusions to the axis of the vagus nerve. Typically, protrusions 49 are relatively short (as shown). The distance between the ends of protrusions 49 and the center of the vagus nerve is typically between about 1 and 3 millimeters. (Generally, the diameter of the vagus nerve is between about 2 and 3 millimeters). Alternatively, for some applications, protrusions 49 are longer and/or the electrodes are placed closer to the vagus nerve in order to reduce the energy consumption of electrode device 22.

In an embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from the plurality of anodes generally minimizes the "virtual cathode effect," whereby application of too large an anodal current stimulates rather than blocks fibers. In an embodiment, anode 44a applies a current with an amplitude equal to about 0.5 to about 5 milliamps (typically one-third of the amplitude of the current applied by anode 44b).

Anode 44a is typically positioned in cuff 48 to apply current at the location on vagus nerve 24 where the virtual cathode effect is maximally generated by anode 44b. For applications in which the blocking current through anode 44b is expected to vary substantially, efferent anode set 44 typically comprises a plurality of virtual-cathode-inhibiting anodes 44a, one or more of which is activated at any time based on the expected magnitude and location of the virtual cathode effect.

Likewise, afferent anode set 45 typically comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

Figure 2B:
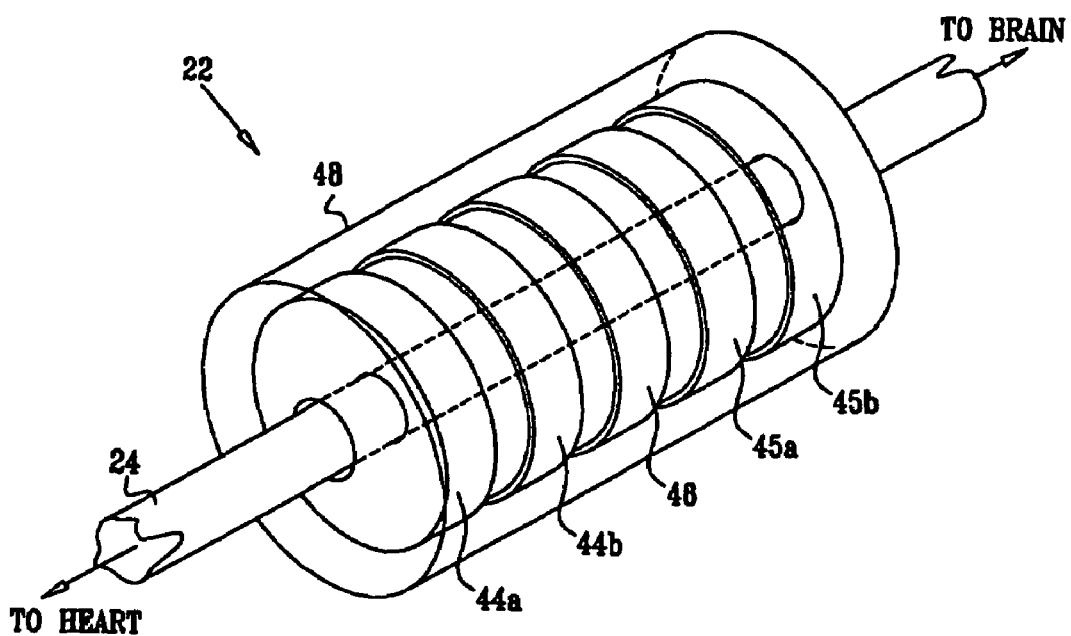
FIG. 2B is a simplified perspective illustration of the electrode device of FIG. 2A, in accordance with an embodiment of the present invention.

FIG. 2B is a simplified perspective illustration of electrode device 22, in accordance with an embodiment of the present invention. When applied to vagus nerve 24, electrode device 22 typically encompasses the nerve. As described, control unit 32 typically drives electrode device 22 to (a) apply signals to vagus nerve 24 in order to induce the propagation of efferent action potentials towards heart 28, and (b) suppress artificially-induced afferent action potentials towards brain 35. The electrodes typically comprise ring electrodes adapted to apply a generally uniform current around the circumference of the nerve, as best shown in FIG. 2B.

Figure 3:
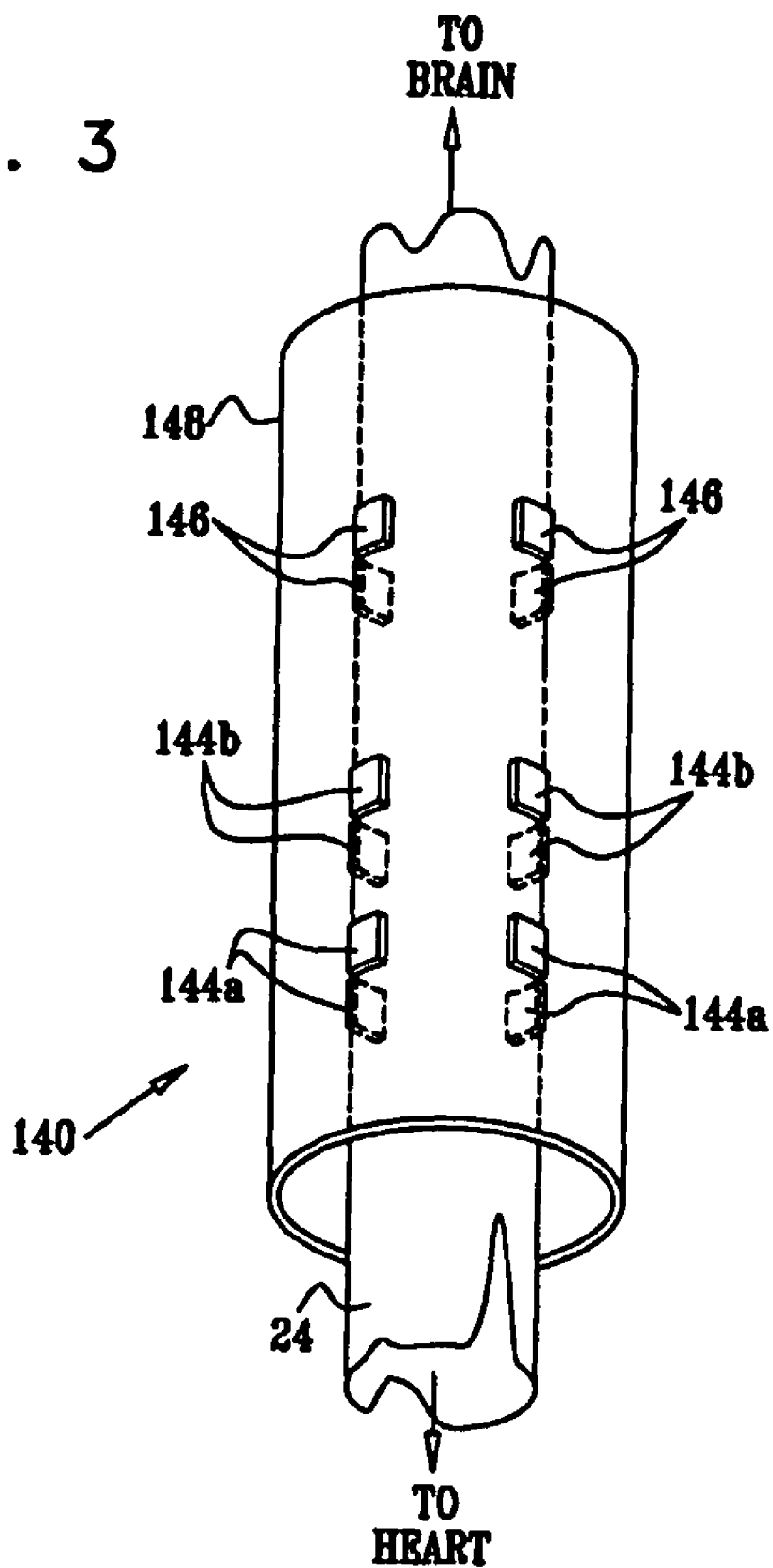
FIG. 3 is a simplified perspective illustration of a multipolar point electrode device applied to a vagus nerve, in accordance with an embodiment of the present invention.

FIG. 3 is a simplified perspective illustration of a multipolar point electrode device 140 applied to vagus nerve 24, in accordance with an embodiment of the present invention. In this embodiment, anodes 144a and 144b and a cathode 146 typically comprise point electrodes (typically 2 to 100), fixed inside an insulating cuff 148 and arranged around vagus nerve 24 so as to selectively stimulate nerve fibers according to their positions inside the nerve. In this case, techniques described in the above-cited articles by Grill et al., Goodall et al., and/or Veraart et al. may be used. The point electrodes typically have a surface area between about 0.01 mm2 and 1 mm2. In some applications, the point electrodes are in contact with vagus nerve 24, as shown, while in other applications the point electrodes are recessed in cuff 148, so as not to come in direct contact with vagus nerve 24, similar to the recessed ring electrode arrangement described above with reference to FIG. 2A. For some applications, one or more of the electrodes, such as cathode 146 or anode 144a, comprise a ring electrode, as described with reference to FIG. 2B, such that electrode device 140 comprises both ring electrode(s) and point electrodes (configuration not shown). Additionally, electrode device 22 optionally comprises an afferent anode set (positioned like anodes 45a and 45b in FIG. 2A), the anodes of which comprise point electrodes and/or ring electrodes.

Alternatively, ordinary, non-cuff electrodes are used, such as when the electrodes are placed on the epicardial fat pads instead of on the vagus nerve.

Figure 4:
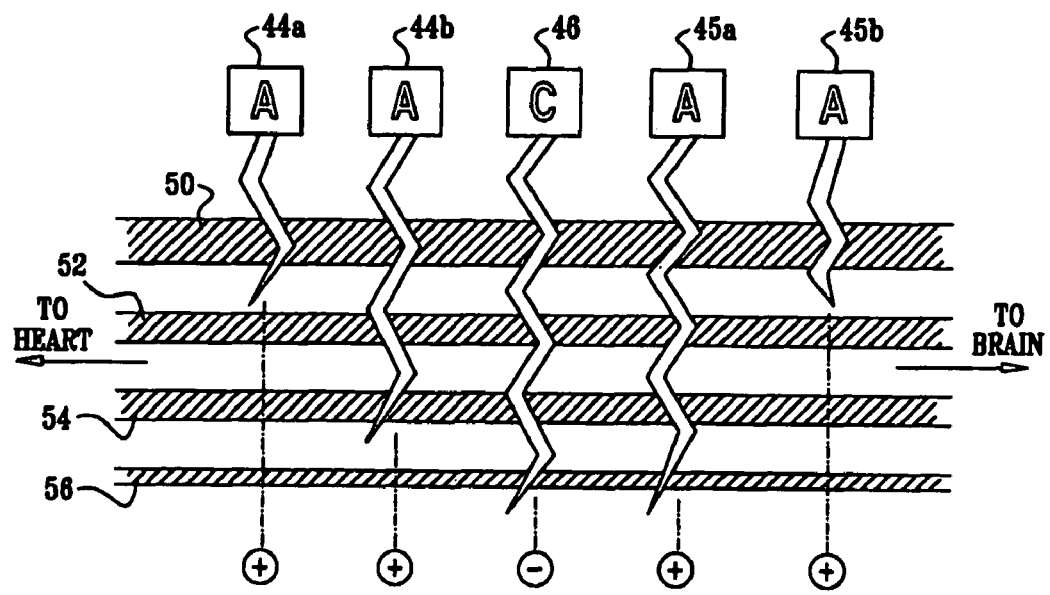
FIG. 4 is a conceptual illustration of the application of current to a vagus nerve, in accordance with an embodiment of the present invention.

FIG. 4 is a conceptual illustration of the application of current to vagus nerve 24 in order to achieve smaller-to-larger diameter fiber recruitment, in accordance with an embodiment of the present invention. When inducing efferent action potentials towards heart 28, control unit 32 drives electrode device 22 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Typically, in order to achieve this recruitment order, the control unit stimulates myelinated fibers essentially of all diameters using cathodic current from cathode 46, while simultaneously inhibiting fibers in a larger-to-smaller diameter order using efferent anodal current from efferent anode set 44. For example, FIG. 4 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 28. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. Alternatively or additionally, in order to increase the number of fibers stimulated, while simultaneously decreasing the average diameter of fibers stimulated, the amplitudes of the currents applied by cathode 46 and efferent anode set 44 are both increased (thereby increasing both the number of fibers stimulated and number of fibers blocked). In addition, for any given number of fibers stimulated (and not blocked), the amount of stimulation delivered to the heart can be increased by increasing the PPT, frequency, and/or pulse width of the current applied to vagus nerve 24.

In order to suppress artificially-induced afferent action potentials from traveling towards the brain in response to the cathodic stimulation, control unit 32 typically drives electrode device 22 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In an embodiment of the present invention, the amplitude of the cathodic current applied in the vicinity of the vagus nerve is between about 2 milliamps and about 10 milliamps. Such a current is typically used in embodiments that employ techniques for achieving generally uniform stimulation of the vagus nerve, i.e., stimulation in which the stimulation applied to fibers on or near the surface of the vagus nerve is generally no more than about 400% greater than stimulation applied to fibers situated more deeply in the nerve. This corresponds to stimulation in which the value of the activation function at fibers on or near the surface of the vagus nerve is generally no more than about four times greater than the value of the activation function at fibers situated more deeply in the nerve. For example, as described hereinabove with reference to FIG. 2A, the electrodes may be recessed so as not to come in direct contact with vagus nerve 24, in order to achieve generally uniform values of the activation function. Typically, but not necessarily, embodiments using approximately 5 mA of cathodic current have the various electrodes disposed approximately 0.5 to 2.5 mm from the axis of the vagus nerve. Alternatively, larger cathodic currents (e.g., 10-30 mA) are used in combination with electrode distances from the axis of the vagus nerve of greater than 2.5 mm (e.g., 2.5-4.0 mm), so as to achieve an even greater level of uniformity of stimulation of fibers in the vagus nerve.

In an embodiment of the present invention, the cathodic current is applied by cathode 46 with an amplitude sufficient to induce action potentials in large- and medium-diameter fibers 50, 52, and 54 (e.g., A- and B-fibers), but insufficient to induce action potentials in small-diameter fibers 56 (e.g., C-fibers). Simultaneously, an anodal current is applied by anode 44b in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked by anode 45a, as described above. Alternatively, the afferent anodal current is configured to not fully block afferent action potentials, or is simply not applied. In these cases, artificial afferent action potentials are nevertheless generally not generated in C-fibers, because the applied cathodic current is not strong enough to generate action potentials in these fibers.

These techniques for efferent stimulation of only B-fibers are typically used in combination with techniques described hereinabove for achieving generally uniform stimulation of the vagus nerve. Such generally uniform stimulation enables the use of a cathodic current sufficiently weak to avoid stimulation of C-fibers near the surface of the nerve, while still sufficiently strong to stimulate B-fibers, including B-fibers situated more deeply in the nerve, i.e., near the center of the nerve. For some applications, when employing such techniques for achieving generally uniform stimulation of the vagus nerve, the amplitude of the cathodic current applied by cathode 46 may be between about 3 and about 10 milliamps, and the amplitude of the anodal current applied by anode 44b may be between about 1 and about 7 milliamps.

For some applications, control unit 32 is adapted to receive feedback from one or more of the electrodes in electrode device 22, and to regulate the signals applied to the electrode device responsive thereto. For example, control unit 32 may analyze amplitudes of various peaks in a compound action potential (CAP) signal recorded by the electrodes, in order to determine a relative proportion of stimulated larger fibers (having faster conduction velocities) to smaller fibers (having slower conduction velocities). Alternatively or additionally, control unit 32 analyzes an area of the CAP, in order to determine an overall effect of the stimulation. In an embodiment, the feedback is received by electrodes other than those used to apply signals to the nerve.

Figure 5:
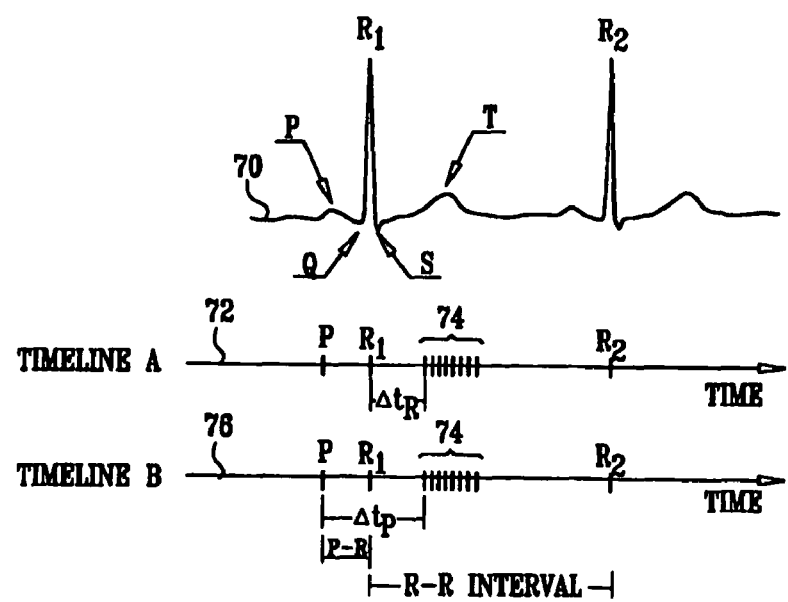
FIG. 5 is a simplified illustration of an electrocardiogram (ECG) recording and of example timelines showing the timing of the application of a series of stimulation pulses, in accordance with an embodiment of the present invention.

FIG. 5 is a simplified illustration of an ECG recording 70 and example timelines 72 and 76 showing the timing of the application of a burst of stimulation pulses 74, in accordance with an embodiment of the present invention. The application of the burst of pulses in each cardiac cycle typically commences after a variable delay after a detected R-wave, P-wave, or other feature of an ECG. For some applications, other parameters of the applied burst of pulses are also varied in real time. Such other parameters include amplitude, pulses per trigger (PPT), pulse duration, and pulse repetition interval. For some applications, the delay and/or one or more of the other parameters are calculated in real time using a function, the inputs of which include one or more pre-programmed but updateable constants and one or more sensed parameters, such as the R-R interval between cardiac cycles and/or the P-R interval.

The variable delay before applying pulse burst 74 in each cardiac cycle can be measured from a number of sensed physiological parameters ("initiation physiological parameters"), including sensed points in the cardiac cycle, including P-, Q-, R-, S- and T-waves. Typically the delay is measured from the P-wave, which indicates atrial contraction. Alternatively, the delay is measured from the R-wave, particularly when the P-wave is not easily detected. Timeline A 72 and Timeline B 76 show the delays, $dt_R$ and $dt_P$ measured from R and P, respectively.

In an embodiment, a lookup table of parameters, such as delays (e.g., dt) and/or other parameters, is used to determine in real time the appropriate parameters for each application of pulses, based on the one or more sensed parameters, and/or based on a predetermined sequence stored in the lookup table.

Optionally, the stimulation applied by vagal stimulation apparatus 20 is applied in conjunction with or separately from stimulation of sympathetic nerves innervating the heart. For example, vagal inhibition described herein and/or periods of non-stimulation of the vagus nerve described herein may be replaced or supplemented by excitation of sympathetic nerves. Such sympathetic stimulation can be applied using techniques of smaller-to-larger diameter fiber recruitment, as described herein, or other nerve stimulation techniques known in the art. For some applications, vagal stimulation is applied in conjunction with stimulation of sympathetic nerves in order to increase vagal tone while minimizing the heart-rate-lowering effect of the vagal stimulation.

Alternatively or additionally, the techniques of smaller-to-larger diameter fiber recruitment are applied in conjunction with methods and apparatus described in one or more of the patents, patent applications, articles and books cited herein.

Figure 6:
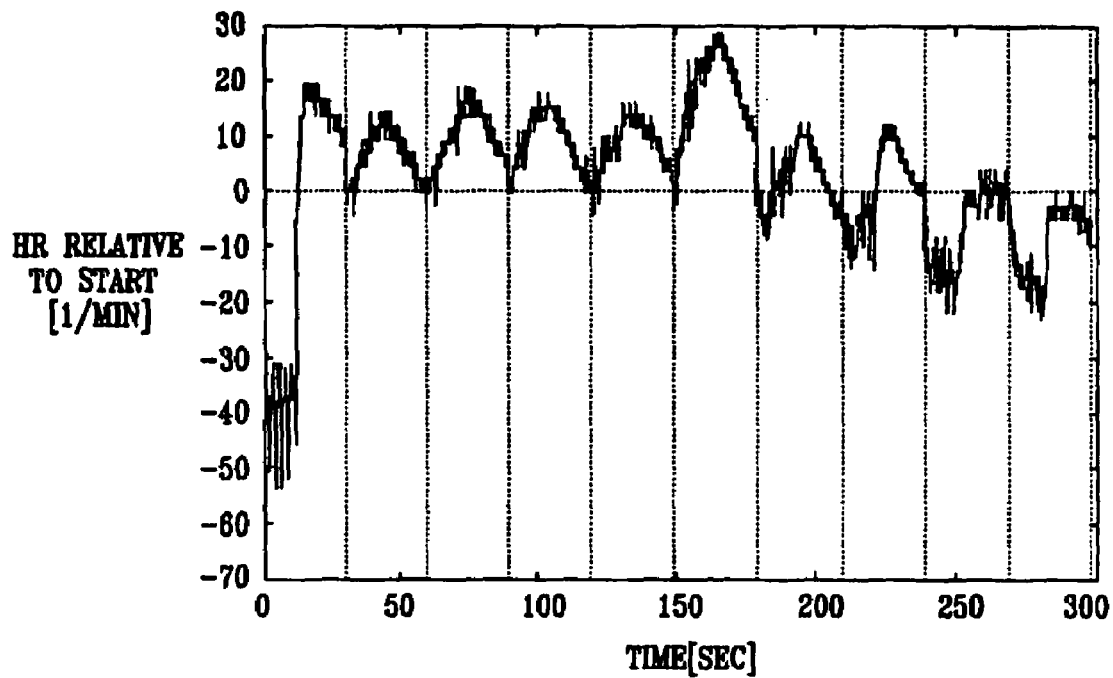
FIGS. 6 and 7 are graphs showing in vivo experimental results measured in accordance with an embodiment of the present invention.

Reference is now made to FIG. 6, which is a graph showing in vivo experimental results measured in accordance with an embodiment of the present invention. A SABAR white rat, weighing 350 g, was anesthetized with Phenobarbital; no other medications were administered. Vagal stimulation was applied using a silver chloride hook electrode immersed in oil placed over the right vagus nerve.

The graph of FIG. 6 shows change in heart rate vs. baseline heart rate, as measured over a 300 second period. During the entire period of the experiment, vagal stimulation was applied in 500 microsecond pulses having an amplitude of 4 mA, at a frequency of 8 Hz. The stimulation was not synchronized with the cardiac cycle of the animal. Beginning at 0 seconds, and concluding at about 12 seconds, 0.8 mg per kg body weight of atropine was administered by intravenous injection to the tail vein.

During the approximately 12 seconds of atropine administration, prior to the atropine taking effect, vagal stimulation is seen demonstrating its expected heart-rate lowering effect, which is attributable to the parasympathetic effect of such stimulation. However, beginning at approximately 13 seconds, with the onset of the effectiveness of the atropine, the heart rate suddenly increased to a level that varied between about 0 and about 20 beats per minute greater than baseline heart rate. This increase is attributed to the fact that vagal stimulation generally has both a parasympathetic and adrenergic effect. Under normal circumstances, the parasympathetic effect dominates the adrenergic effect. However, when the parasympathetic effect is blocked, such as by atropine, the adrenergic effect is expressed, resulting in increased heart rate, among other effects. Beginning at about 180 seconds, as the atropine-induced parasympathetic blockade faded, the parasympathetic effect of stimulation again began to dominate, resulting in a reduced heart rate.

It is believed by the inventors that these experimental results at least in part explain the effectiveness of the minimal heart rate reduction stimulation described hereinabove. During stimulation with such parameters, the heart-rate-lowering effects of vagal stimulation are nearly offset by the adrenergic effects of the vagal stimulation. Nevertheless, the parasympathetic nervous system is still activated, resulting in the beneficial effects of such stimulation described hereinabove.

Figure 7:
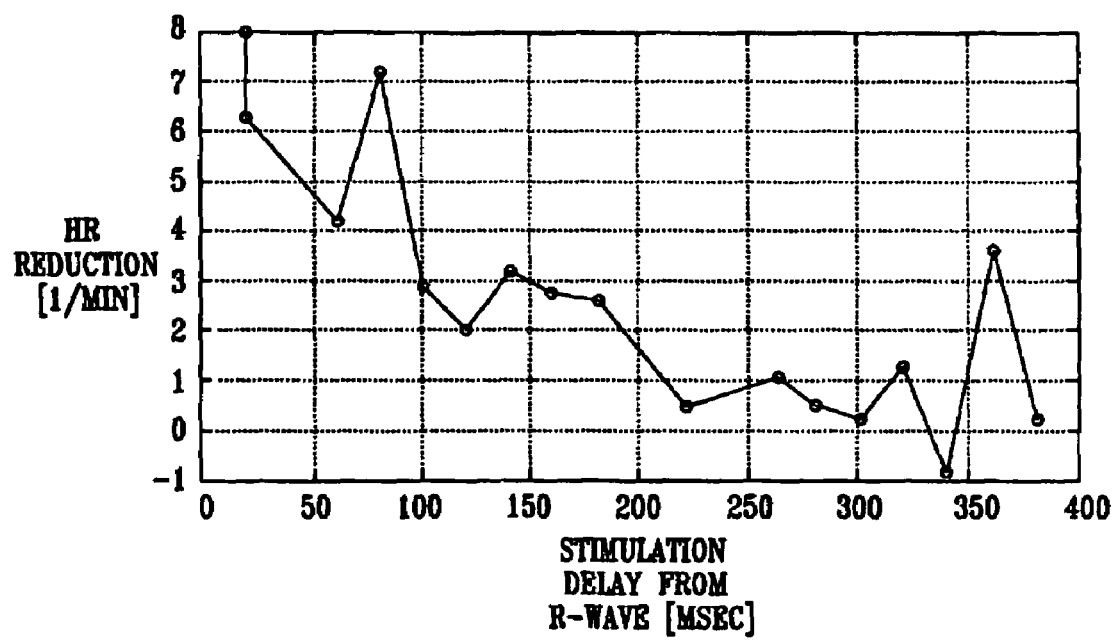

FIG. 7 is a graph showing in vivo experimental results measured in accordance with an embodiment of the present invention. A male dog, weighing 25 kg, was initially anesthetized with propafol; anesthesia was maintained with inhaled gas isoflurane. The dog was mechanically ventilated. The right vagus nerve was stimulated using a tripolar cuff electrode in an anode-cathode-anode configuration, with the anodes shorted to each other, similar to the shorted anode configuration described hereinabove with reference to FIG. 2A. The cuff electrode was immersed in normal saline solution.

The graph of FIG. 7 shows heart rate reduction vs. baseline (with reduction expressed by positive values) responsive to vagal stimulation applied after different delays from the R-wave. Baseline heart rate was calculated based on the average interval between beats prior to beginning stimulation. For each data point, the heart rate was calculated as the time interval between the second and third beat after application of the stimulation. The reduction in heart rate caused by the stimulation is shown on the y-axis. As is seen in the graph, longer delays from the R-wave generally resulted in less heart rate reduction. Delays of at least 200 milliseconds resulted in substantially no reduction in heart rate. It is believed by the inventors that these data support the timing parameters of the minimal heart rate reduction stimulation described hereinabove. It is hypothesized by the inventors that for each of the delays shown, total acetylcholine release is substantially the same. In support of this hypothesis, it is noted that acetylcholine is released in efferent fibers in response to the applied vagal stimulation, but is expected to be largely (or entirely) unaffected in these fibers by the precise timing of the cardiac cycle, because these fibers do not receive input from the heart. Because acetylcholine release is an indication of the level of parasympathetic stimulation, this hypothesis as well as the experimental results indicate that vagal stimulation, with delays chosen in accordance with this embodiment, has little or no effect on heart rate, while maintaining substantially the same effect on the parasympathetic nervous system.

In an embodiment of the present invention, a calibration period is provided to determine a delay for each patient that generally corresponds to, for example, the 200 ms delay shown in the figure, and this determined delay is applied to allow vagal stimulation with minimal heart rate reduction in the patient.

Figure 8:
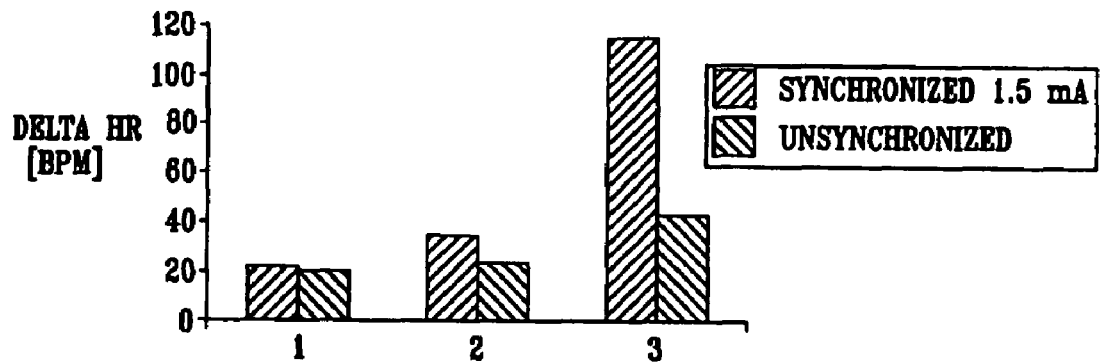
FIG. 8 is a chart showing in vivo experimental results in accordance with an embodiment of the present invention.

FIG. 8 is a chart showing in vivo experimental results in accordance with an embodiment of the present invention. A SABAR white rat, weighing 350 g, was anesthetized with Phenobarbital. Vagal stimulation was applied using a silver chloride hook electrode immersed in oil placed over the right vagus nerve. Vagal stimulation was applied with an amplitude of 1.5 milliamps. Medications, as described below, were administered intravenously through the tail vein.

The chart of FIG. 8 shows heart rate reductions vs. baseline heart rates (with the reductions expressed by positive values) responsive to vagal stimulation applied alone (bars 1), vagal stimulation applied after administration of 1 mg of the beta-blocker metoprolol (bars 2), and vagal stimulation applied after administration of 0.2 mg of adrenaline (bars 3). (For determining the metoprolol and adrenaline reductions, the respective baselines were measured after the medications had taken effect). The left bar in each pair of bars shows results when vagal stimulation was synchronized with the cardiac cycle, and the right bar shows results with unsynchronized stimulation. As is seen, both the beta-blocker and adrenaline cause vagal stimulation to achieve a greater heart-rate-lowering effect at the same level of stimulation.

Figure 9A:
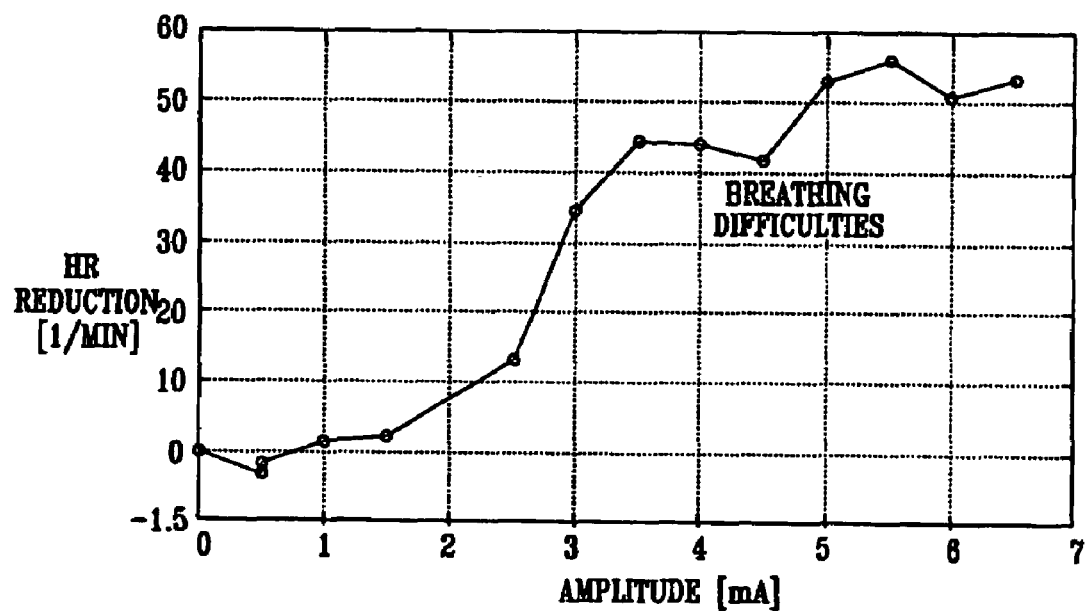
FIGS. 9A and 9B are graphs showing an analysis of the experimental results of the experiment of FIG. 7, in accordance with an embodiment of the present invention.
Figure 9B:
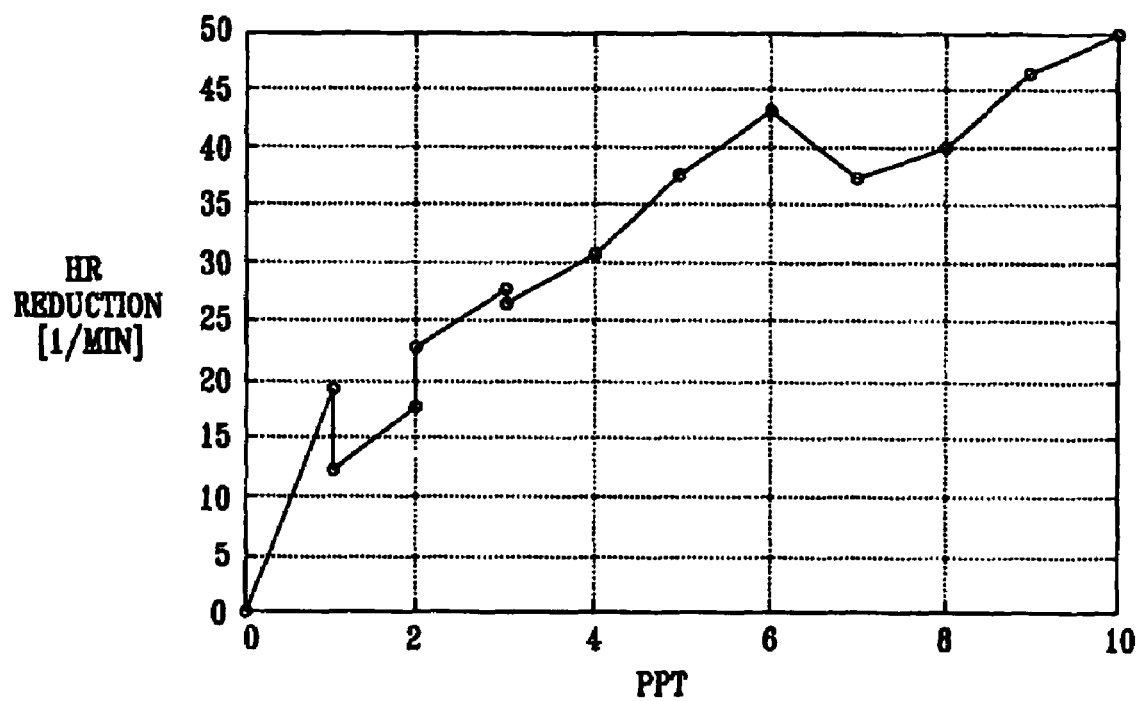

FIGS. 9A and 9B are graphs showing an analysis of the experimental results of the experiment described hereinabove with reference to FIG. 7, in accordance with an embodiment of the present invention. Both graphs show heart rate reduction vs. baseline (with reduction expressed by positive values). However, in FIG. 9A increased reduction was achieved by increasing the amplitude of the applied signal, while in FIG. 9B increased reduction was achieved by increasing the number of pulses per trigger (PPT), i.e., the number of pulses in a pulse train applied once per cardiac cycle. The pulses of the experiment shown in FIG. 9B were applied after a constant delay of 60 ms after each R-wave, synchronized with the cardiac cycle.

Although similar fine control of heart rate reduction was achieved using modulation of both parameters, the animal experienced severe side effects, including breathing difficulties (gasping, belching, hoarseness, and wheezing), when signal amplitude was modulated (FIG. 9A) and the heart rate reduction reached about 40 beats per minute. Substantially no side effects were observed when PPT was modulated. These data suggest that heart rate reduction can be achieved with fewer side effects by varying PPT rather than signal amplitude.

Figure 10A:
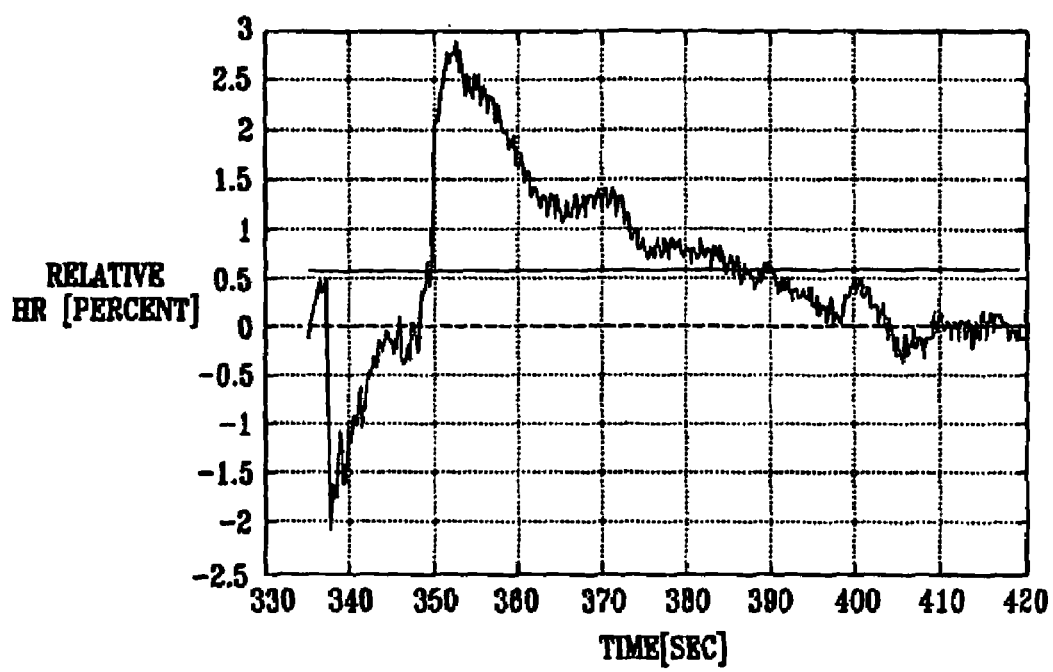
FIGS. 10A and 10B are graphs showing in vivo experimental results in accordance with an embodiment of the present invention.
Figure 10B:
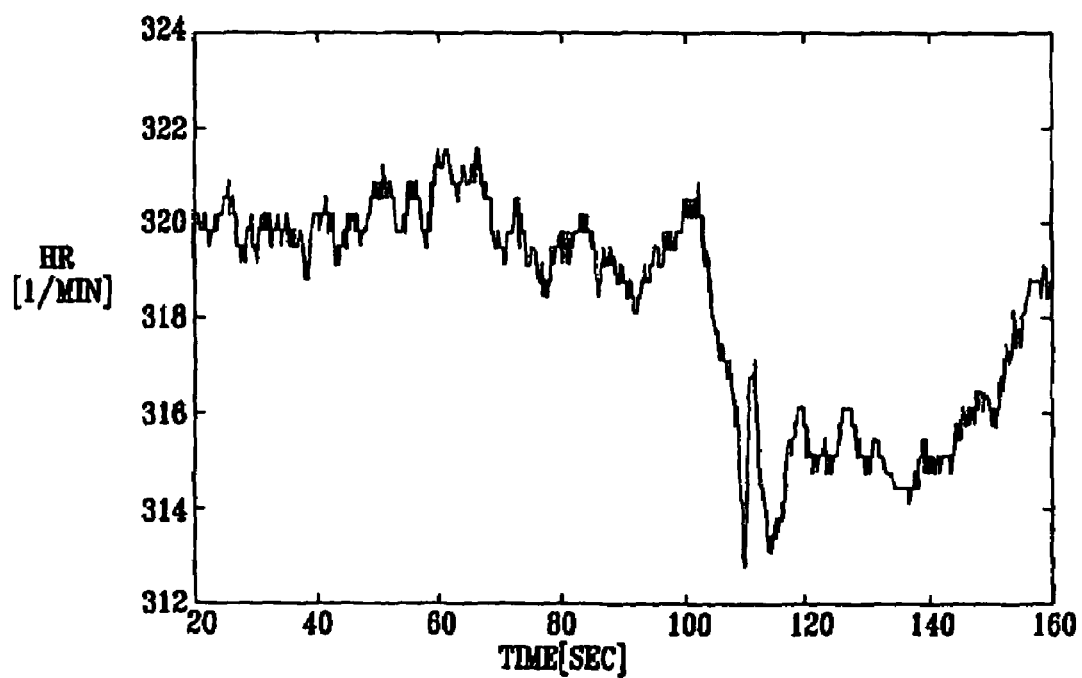

FIGS. 10A and 10B are graphs showing in vivo experimental results in accordance with an embodiment of the present invention. These graphs respectively reflect two different sets of parameters used to achieve vagal stimulation with minimal heart-rate-lowering effects. A SABAR white rat, weighing 350 g, was anesthetized with Phenobarbital; no other medications were administered. Vagal stimulation was applied using a silver chloride hook electrode immersed in oil placed over the right vagus nerve. The heart rate in FIG. 10A is expressed as a percent change from a baseline average heart rate.

The data shown in the graph of FIG. 10A were obtained using the following stimulation parameters: (a) an "on" time of 12.5 seconds (10 triggers), and an "off" time of 110 seconds, (b) 1 pulse per trigger, (c) a stimulation frequency of 0.8 Hz, (d) an amplitude of 2 milliamps, and (e) a pulse width of 500 microseconds. Stimulation was applied between about 336 and about 348.5 seconds. As seen in the graph, the stimulation initially reduced the heart rate (until about 350 seconds). However, upon cessation of stimulation at 348.5 seconds, heart rate increased with rebound strength for about 40 seconds (until about 390 seconds). As a result, the average heart rate caused by stimulation was not substantially different from the average heart rate without stimulation. This lack of substantial difference is illustrated by the two horizontal lines of the graph. The upper line represents the average heart rate during stimulation and the 40 seconds following stimulation (i.e., between 330 and 390 seconds), while the lower line represents the average heart rate excluding these periods (i.e., the average heart rate between 300 and 330 seconds, and between 390 and 420 seconds.

The data shown in the graph of FIG. 10B were obtained using the following stimulation parameters: (a) 1 pulse per trigger, (b) an amplitude of 0.1 mA, and (c) a pulse duration of 500 microseconds. Stimulation was applied at two stimulation time points, the first at 35 seconds and the second at 100 seconds. The stimulation applied at the first point consisted of 4 triggers (i.e., cardiac cycles), while the stimulation applied at the second point consisted of 12 triggers. As is shown on the graph, the stimulation applied at the first point had essentially no heart-rate-lowering effect, while the stimulation applied at the second point substantially lowered the heart rate. These results demonstrate that, mutatis mutandis, the heart-rate-lowering effect of vagal stimulation depends in part upon the length (i.e., number of triggers) of the stimulation. By using a brief stimulation period, vagal stimulation can be achieved while having a minimal or no heart-rate-lowering effect.

Although some embodiments of the present invention are described herein with respect to applying an electrical current to tissue of a patient, this is to be understood in the specification and in the claims as including creating a voltage drop between two or more electrodes.

Although embodiments of the present invention described hereinabove with reference to FIGS. 2A, 2B, 3 and 4 are described with reference to the vagus nerve, the electrode devices of these embodiments may also be applied to other nerves for some applications.

As appropriate, techniques described herein are practiced in conjunction with methods and apparatus described in one or more of the following patent applications, all of which are assigned to the assignee of the present application and are incorporated herein by reference:

U.S. patent application Ser. No. 10/205,474, filed Jul. 24, 2002, entitled, "Electrode assembly for nerve control," which published as US Patent Publication 2003/0050677

U.S. Provisional Patent Application 60/383,157 to Ayal et al., filed May 23, 2002, entitled, "Inverse recruitment for autonomic nerve systems"

U.S. patent application Ser. No. 10/205,475, filed Jul. 24, 2002, entitled, "Selective nerve fiber stimulation for treating heart conditions," which published as US Patent Publication 2003/0045909

PCT Patent Application PCT/IL02/00068, filed Jan. 23, 2002, entitled, "Treatment of disorders by unidirectional nerve stimulation," and U.S. patent application Ser. No. 10/488,334, filed Feb. 27, 2004, in the US National Phase thereof U.S. patent application Ser. No. 09/944,913, filed Aug. 31, 2001, entitled, "Treatment of disorders by unidirectional nerve stimulation"

U.S. patent application Ser. No. 10/461,696, filed Jun. 13, 2003, entitled, "Vagal stimulation for anti-embolic therapy"

PCT Patent Application PCT/IL03/00430, filed May 23, 2003, entitled, "Electrode assembly for nerve control," which published as PCT Publication WO 03/099373

PCT Patent Application PCT/IL03/00431, filed May 23, 2003, entitled, "Selective nerve fiber stimulation for treating heart conditions," which published as PCT Publication WO 03/099377

U.S. patent application Ser. No. 10/719,659, filed Nov. 20, 2003, entitled, "Selective nerve fiber stimulation for treating heart conditions"

A PCT patent application filed May 23, 2004, entitled, "Selective nerve fiber stimulation for treating heart conditions"

A PCT patent application filed on even date herewith, entitled, "Vagal stimulation for anti-embolic therapy"

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:

administering, to a subject susceptible to bradycardia, a beta-blocker at a dosage lower than would normally be indicated for the subject;

applying a current to a site of the subject selected from the group of sites consisting of: a vagus nerve of the subject, an epicardial fat pad of the subject, a pulmonary vein of the subject, a carotid artery of the subject, a carotid sinus of the subject, a vena cava vein of the subject, and an internal jugular vein of the subject;

sensing a heart rate of the subject; and upon detecting an occurrence of the bradycardia, terminating applying the current at least until a cessation of the bradycardia.

2. The method according to claim 1, wherein applying the current comprises applying the current in respective bursts of pulses in each of a plurality of cardiac cycles of the subject.

3. The method according to claim 2, wherein applying the current comprises synchronizing the bursts with a cardiac cycle of the subject.

4. The method according to claim 2, wherein applying the current comprises applying a first pulse of each of the bursts after a delay from a sensed feature of an electrocardiogram (ECG) of the subject.

5. The method according to claim 2, wherein applying the current comprises configuring each of the pulses to have a duration of between about 100 microseconds and about 2.5 milliseconds.

6. The method according to claim 1, wherein applying the current comprises configuring the current so as to have an antiarrhythmic effect on an atrium of the subject.

7. The method according to claim 1, wherein applying the current comprises configuring the current to inhibit propagation of naturally-generated efferent action potentials traveling through the site.

8. The method according to claim 7, wherein applying the current comprises applying the current to the vagus nerve.

9. The method according to claim 1, wherein the subject suffers from heart failure, and wherein administering comprises administering the beta-blocker to the subject suffering from the heart failure.

10. The method according to claim 1, wherein applying the current comprises configuring the current at least in part responsively to the sensed heart rate.

11. The method according to claim 1, wherein applying the current comprises configuring one or more parameters of the current so as to minimize a heart-rate-lowering effect of the applying of the current.

* * * * *